United States Patent
Okamoto et al.

(10) Patent No.: US 12,280,194 B2
(45) Date of Patent: *Apr. 22, 2025

(54) PRESSURE DETECTOR

(71) Applicant: Nikkiso Company Limited, Tokyo (JP)

(72) Inventors: Shingo Okamoto, Shizuoka (JP); Hiroyuki Kawajiri, Shizuoka (JP); Ryo Kato, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 951 days.

This patent is subject to a terminal disclaimer.

(21) Appl. No.: 17/093,817

(22) Filed: Nov. 10, 2020

(65) Prior Publication Data

US 2021/0052800 A1    Feb. 25, 2021

Related U.S. Application Data

(63) Continuation of application No. PCT/JP2019/019393, filed on May 15, 2019.

(30) Foreign Application Priority Data

May 16, 2018    (JP) .................................. 2018-094462

(51) Int. Cl.
    *A61M 1/36*     (2006.01)
    *A61M 1/16*     (2006.01)

(52) U.S. Cl.
    CPC ........ *A61M 1/3639* (2013.01); *A61M 1/1601* (2014.02); *A61M 1/3607* (2014.02); *A61M 2205/3344* (2013.01)

(58) Field of Classification Search
    CPC .............. A61M 1/3639; A61M 1/1601; A61M 1/3607; A61M 1/3641; A61M 1/36;
(Continued)

(56) References Cited

U.S. PATENT DOCUMENTS

| 4,908,493 A | 3/1990 | Susemihl |
| 5,221,271 A | 6/1993 | Nicholson et al. |

(Continued)

FOREIGN PATENT DOCUMENTS

| DE | 102008034920 A1 | 9/2009 |
| EP | 0074733 A1 | 3/1983 |

(Continued)

OTHER PUBLICATIONS

International Search Report dated Jun. 11, 2019 for Application No. PCT/JP2019/019393 published as WO2019221202.

(Continued)

*Primary Examiner* — Akash K Varma
(74) *Attorney, Agent, or Firm* — Young Basile Hanlon & MacFarlane, P.C.

(57) ABSTRACT

A pressure detector that includes a case connectable to a flow route for liquid, and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The pressure detector includes an inlet port including a connecting portion connectable to the flow route for the liquid, and a flow-route portion through which the liquid flows into an inlet opening of the liquid-phase portion; and an outlet port including a connecting portion connectable to the flow route for the liquid, and a flow-route portion through which the liquid having flowed into the liquid-phase portion is discharged from an outlet opening. At least one of the flow-route portion of the inlet port and the flow-route portion of the outlet port is configured such that an incoming (Continued)

direction or an outgoing direction of the liquid is inclined with respect to an attaching plane defined for the membrane member.

17 Claims, 14 Drawing Sheets

(58) Field of Classification Search
CPC .. A61M 1/00; A61M 1/16; A61M 2205/3344; G01L 7/082; G01L 7/08; G01L 7/00; G01L 19/0038; G01L 19/143; G01L 19/0023; G01L 19/00; G01L 19/06; G01L 19/14; G01L 11/00
USPC ......................................................... 210/646
See application file for complete search history.

(56) References Cited

U.S. PATENT DOCUMENTS

| | | | |
|---|---|---|---|
| 5,722,946 A | 3/1998 | Mudloff et al. | |
| 6,392,208 B1 | 5/2002 | Arx | |
| 8,092,414 B2 | 1/2012 | Schnell et al. | |
| 8,960,010 B1 | 2/2015 | Crnkovich et al. | |
| 10,775,252 B2 | 9/2020 | Funamura et al. | |
| 2003/0115965 A1 | 6/2003 | Mittelstein et al. | |
| 2004/0050168 A1* | 3/2004 | Uberreiter | A61M 1/3641 73/866.5 |
| 2007/0118153 A1 | 5/2007 | Funamura et al. | |
| 2007/0234817 A1* | 10/2007 | Brucksch | A61M 1/3639 73/756 |
| 2007/0295093 A1 | 12/2007 | Reiter et al. | |
| 2009/0071258 A1 | 3/2009 | Kouda et al. | |
| 2010/0018317 A1* | 1/2010 | Kitani | A61M 1/3644 73/706 |
| 2010/0186518 A1* | 7/2010 | Jonsson | A61M 1/3641 73/756 |
| 2011/0290352 A1 | 12/2011 | Reiter et al. | |
| 2015/0306299 A1* | 10/2015 | Stuva | A61M 1/16 604/121 |
| 2017/0312412 A1 | 11/2017 | Mochizuki | |
| 2017/0340798 A1 | 11/2017 | Lindley et al. | |
| 2020/0198459 A1 | 6/2020 | Bouffier et al. | |
| 2021/0106744 A1 | 4/2021 | Okamoto et al. | |

FOREIGN PATENT DOCUMENTS

| | | |
|---|---|---|
| EP | 0330891 A1 | 9/1989 |
| EP | 1843140 A2 | 10/2007 |
| EP | 2155287 B1 | 10/2017 |
| JP | S62-051630 B2 | 10/1987 |
| JP | H02-001275 A | 1/1990 |
| JP | H09-024026 A | 1/1997 |
| JP | 2008-051663 A | 3/2008 |
| JP | 2008-136673 A | 6/2008 |
| JP | 2010-172739 A | 8/2010 |
| JP | 2014-204779 A | 10/2014 |
| JP | 2015-112223 A | 6/2015 |
| JP | 2016-221028 A | 12/2016 |
| JP | 2017-106812 A | 6/2017 |
| JP | 2019-063439 A | 4/2019 |
| WO | 2007/040223 A1 | 4/2007 |
| WO | 2007/120812 A2 | 10/2007 |
| WO | 2008/106191 A2 | 9/2008 |
| WO | 2014/028103 A1 | 2/2014 |
| WO | 2014/093846 A1 | 6/2014 |
| WO | 2015/099932 A1 | 7/2015 |
| WO | 2017/015322 A1 | 1/2017 |
| WO | 2019221202 A1 | 11/2019 |
| WO | 2019221203 A1 | 11/2019 |
| WO | 2019221204 A1 | 11/2019 |
| WO | 2019221205 A1 | 11/2019 |

OTHER PUBLICATIONS

Potentially related U.S. Appl. No. 15/823,794, filed Nov. 28, 2017 entitled "Medical Liquid-Pressure-Detecting Device", issued as U.S. Pat. No. 10,775,252 on Sep. 15, 2020.
Potentially related U.S. Appl. No. 17/093,821, filed Nov. 10, 2020 entitled "Pressure Detector," Published as WO2019221203.
Potentially related U.S. Appl. No. 17/093,823, filed Nov. 10, 2020 entitled "Pressure Detector," Published as WO2019221204.
Potentially related U.S. Appl. No. 17/093,825, filed Nov. 10, 2020 entitled "Pressure Detector," Published as WO2019221205.
European Search Report for Application No. 19804381.2, dated Nov. 25, 2021.

* cited by examiner

[Fig. 1]
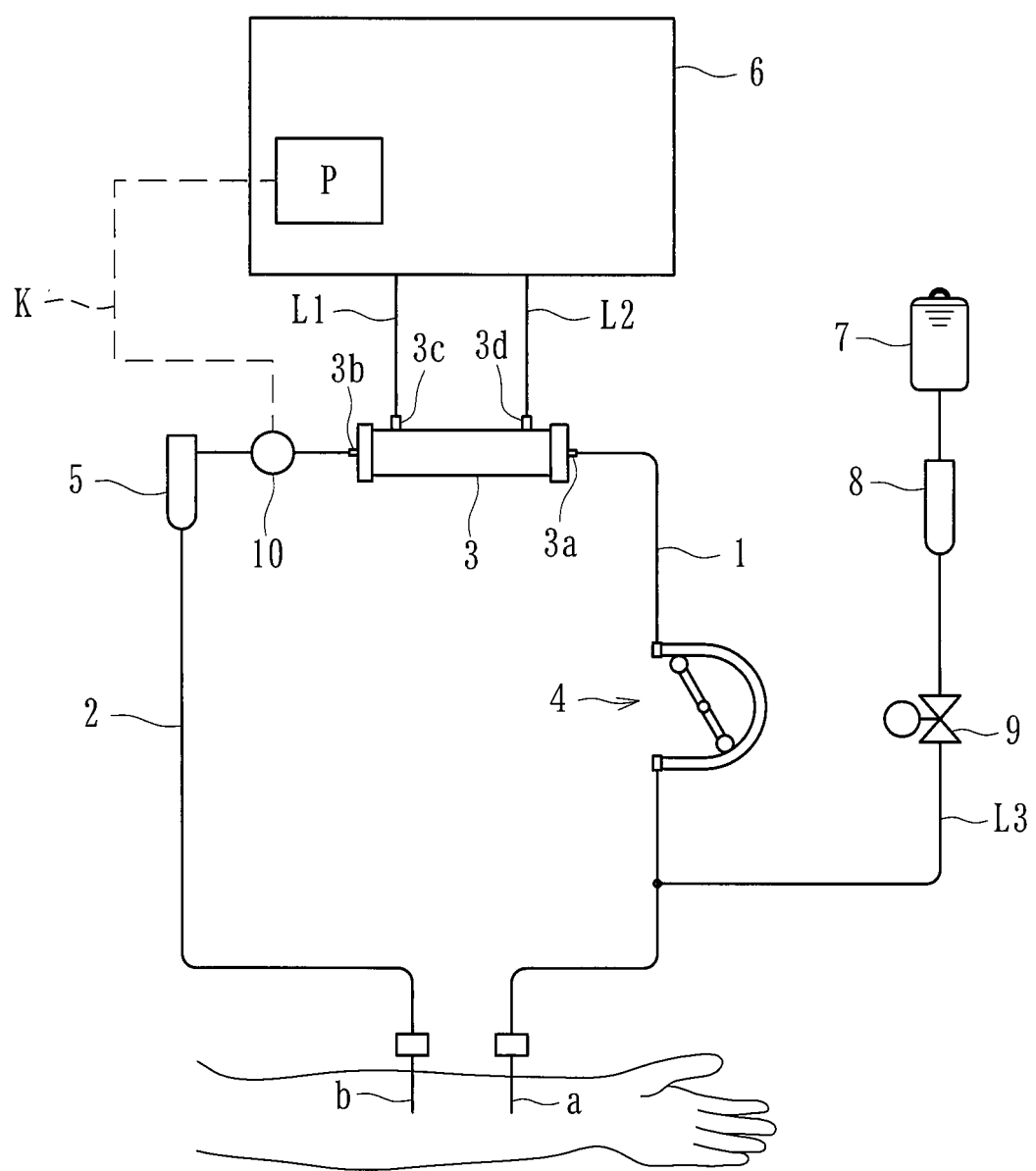

[Fig. 2]
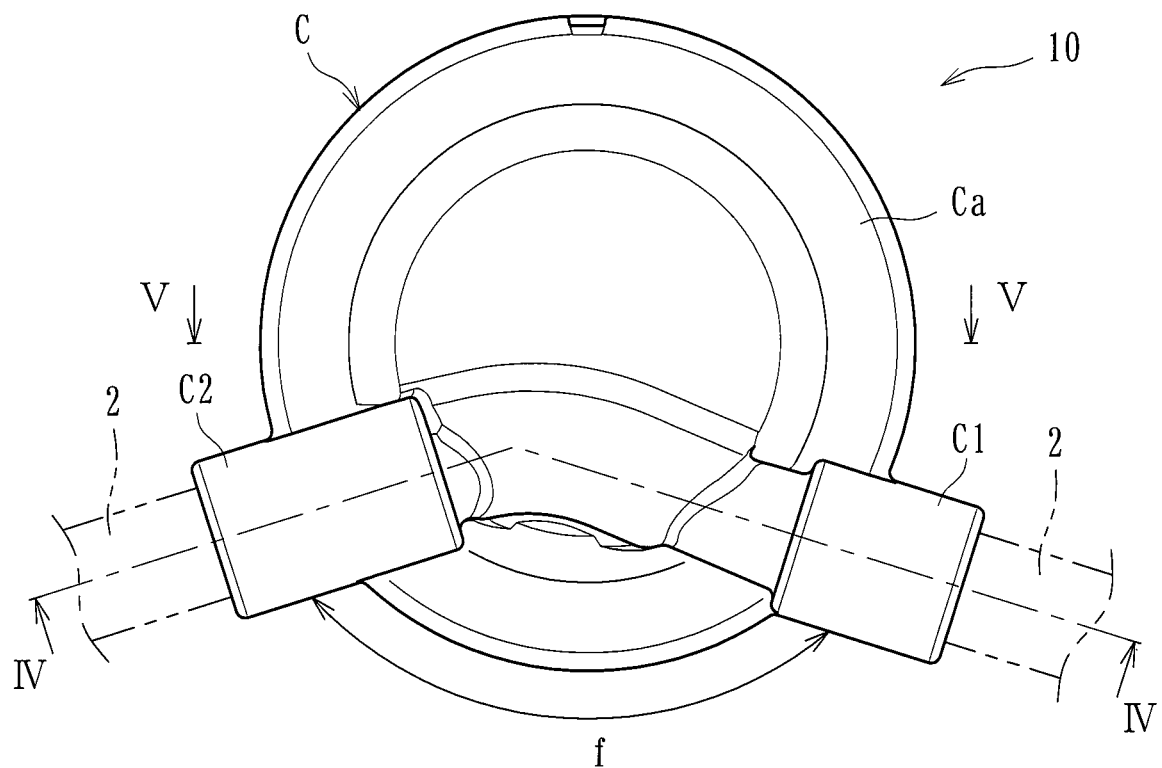
[Fig. 3]
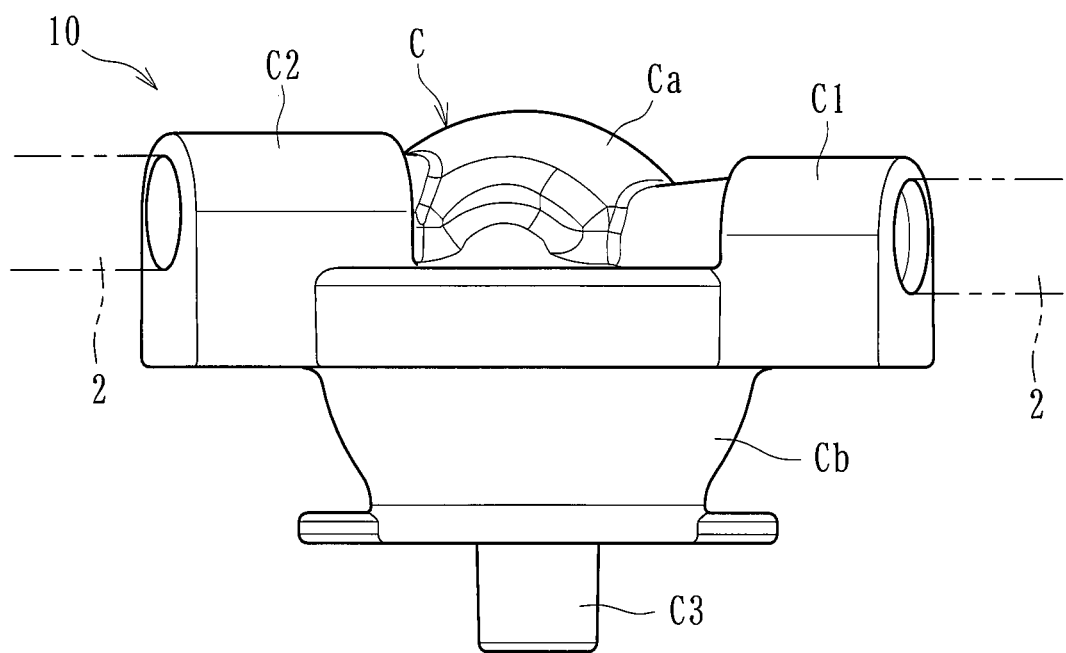

[Fig. 4]
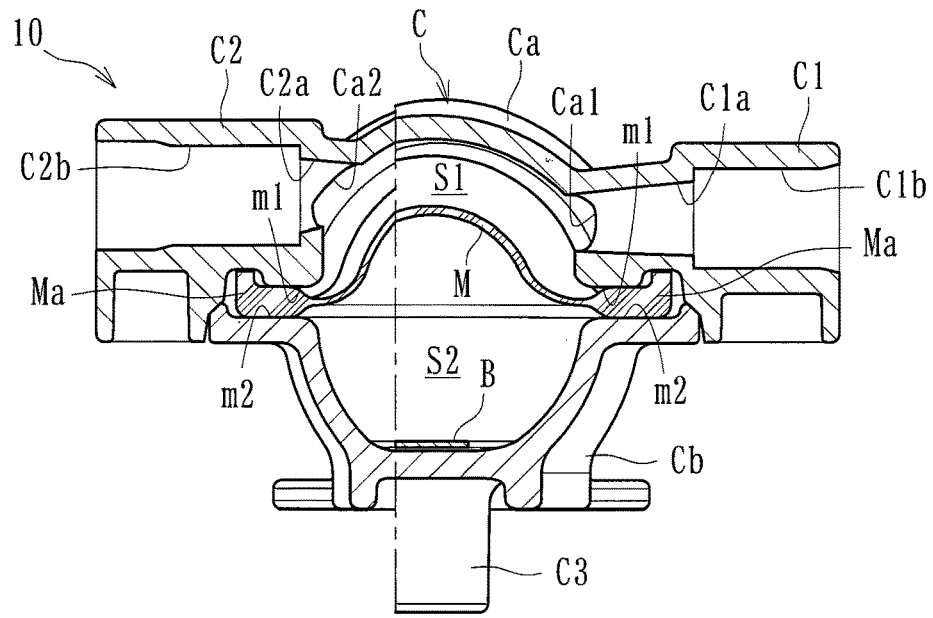
[Fig. 5]
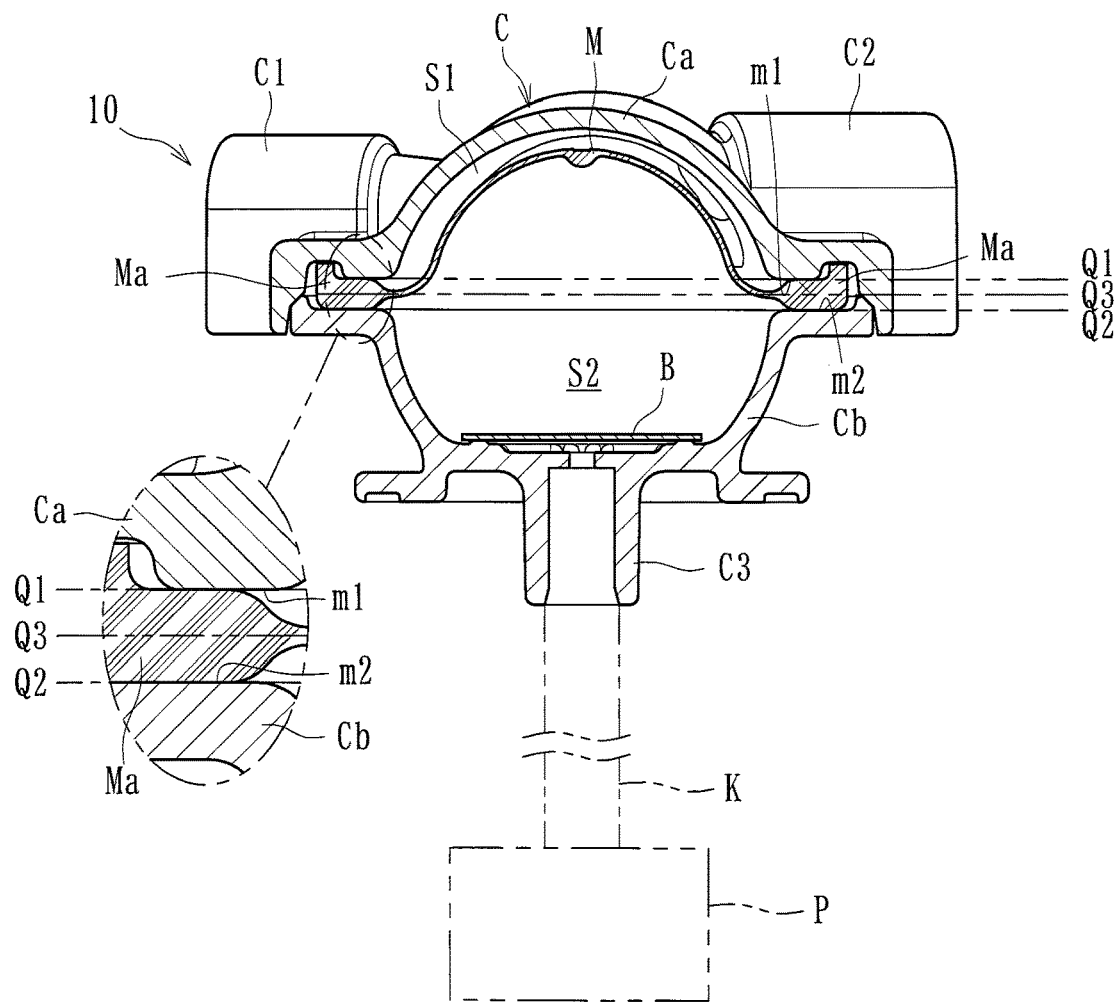

[Fig. 6]
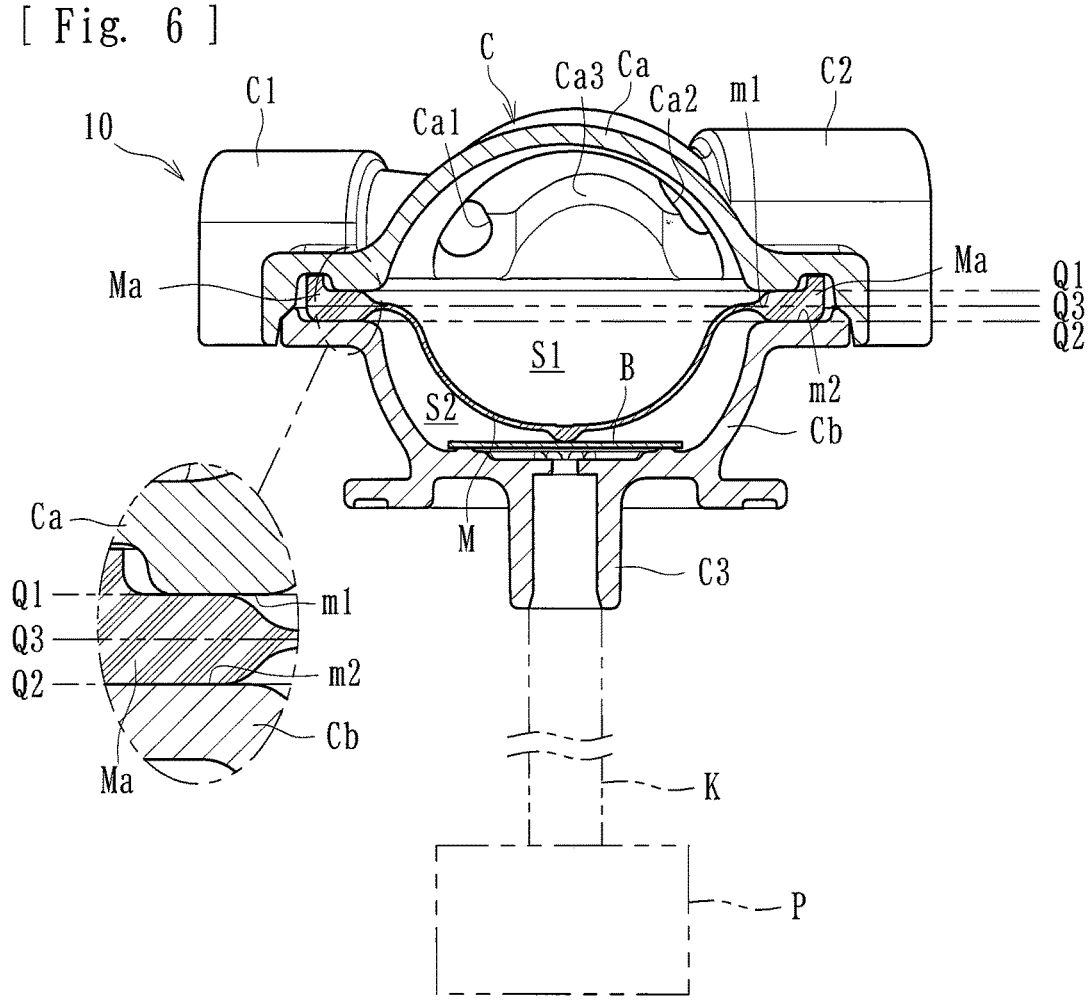
[Fig. 7]
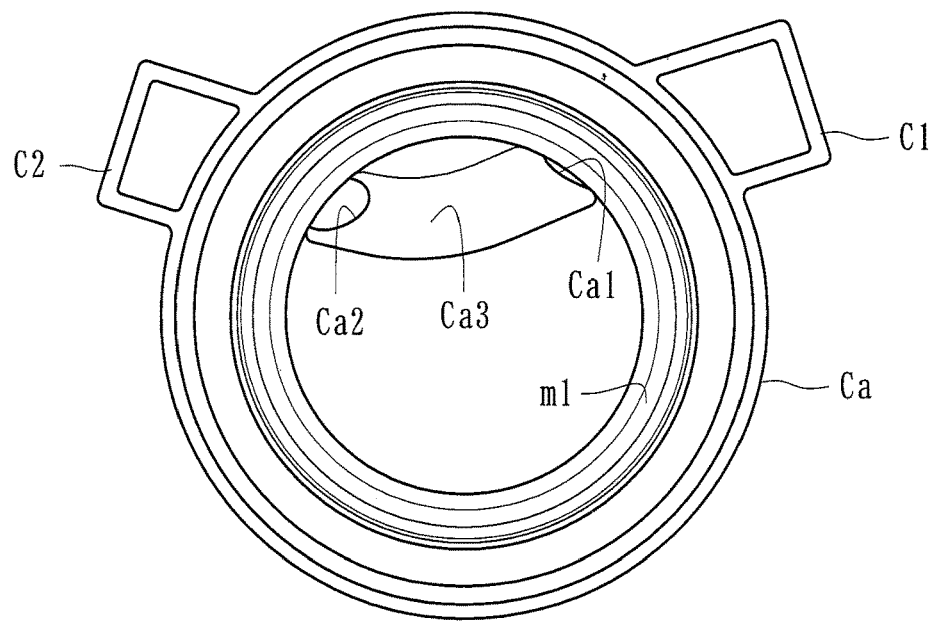

[Fig. 8]
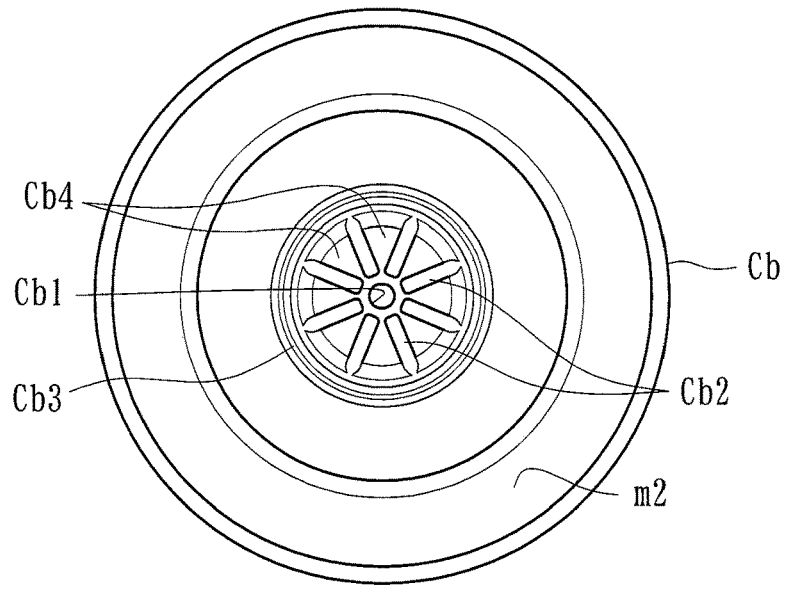
[Fig. 9]
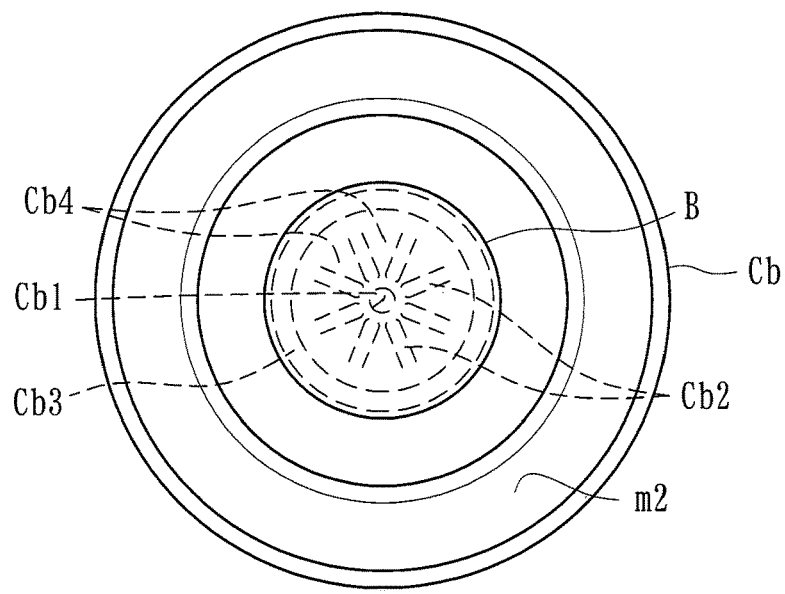
[Fig. 10]
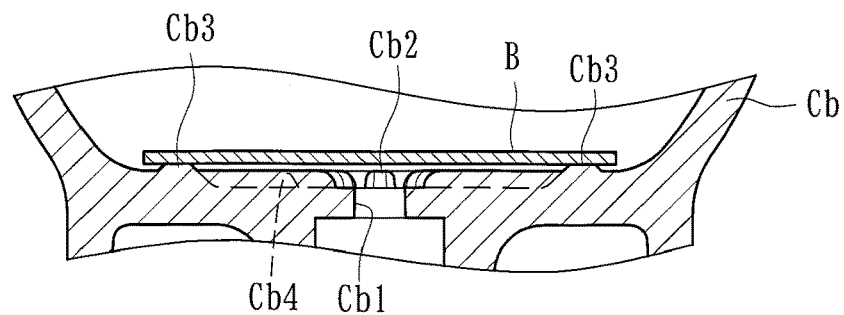

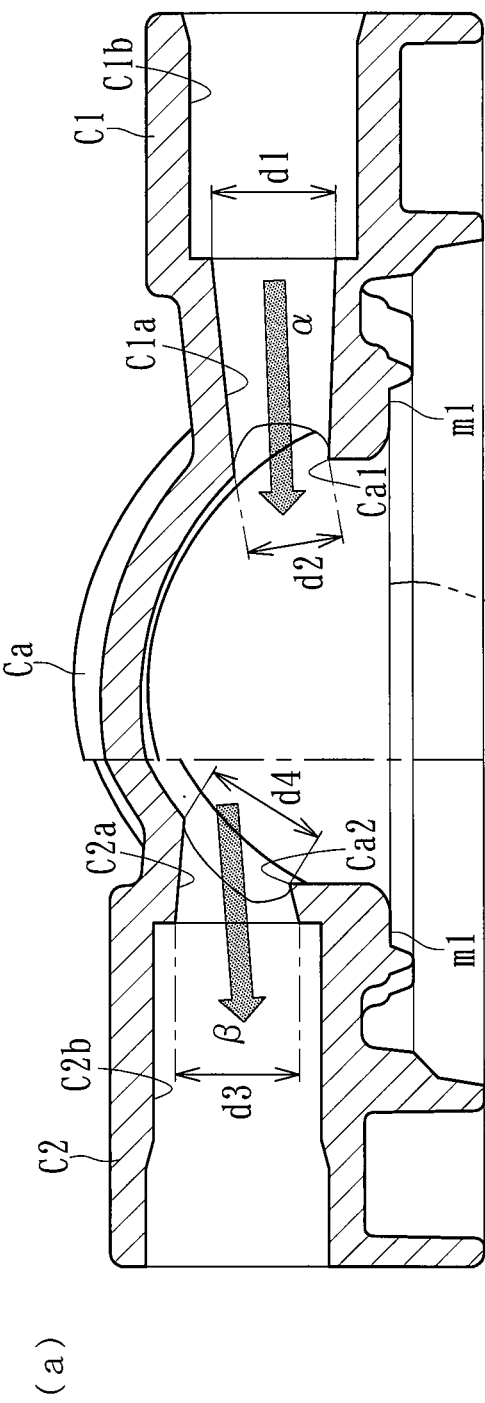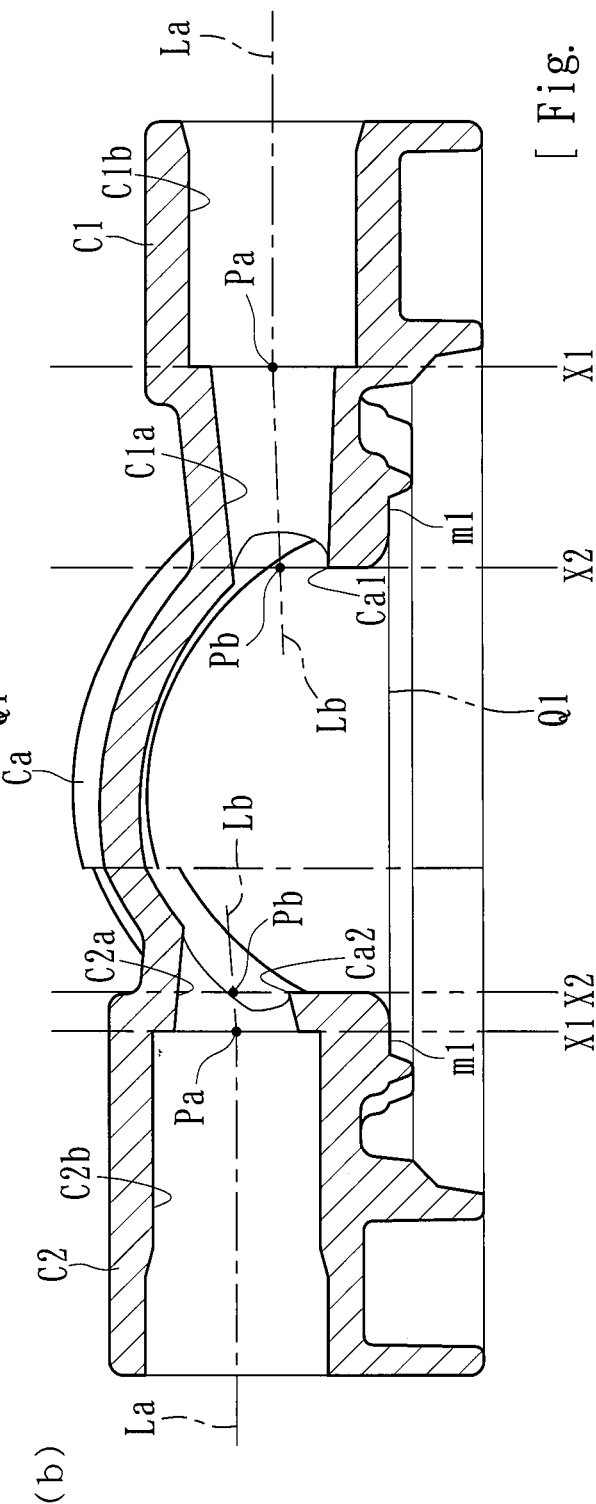
[Fig. 11]

[Fig. 12]
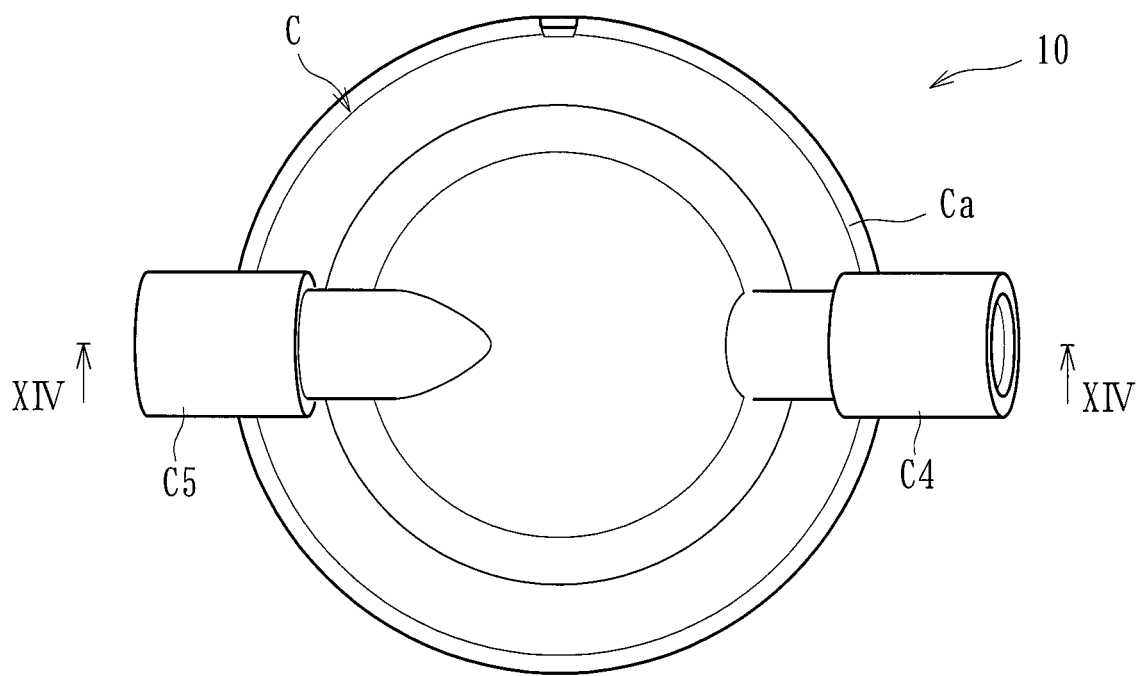
[Fig. 13]
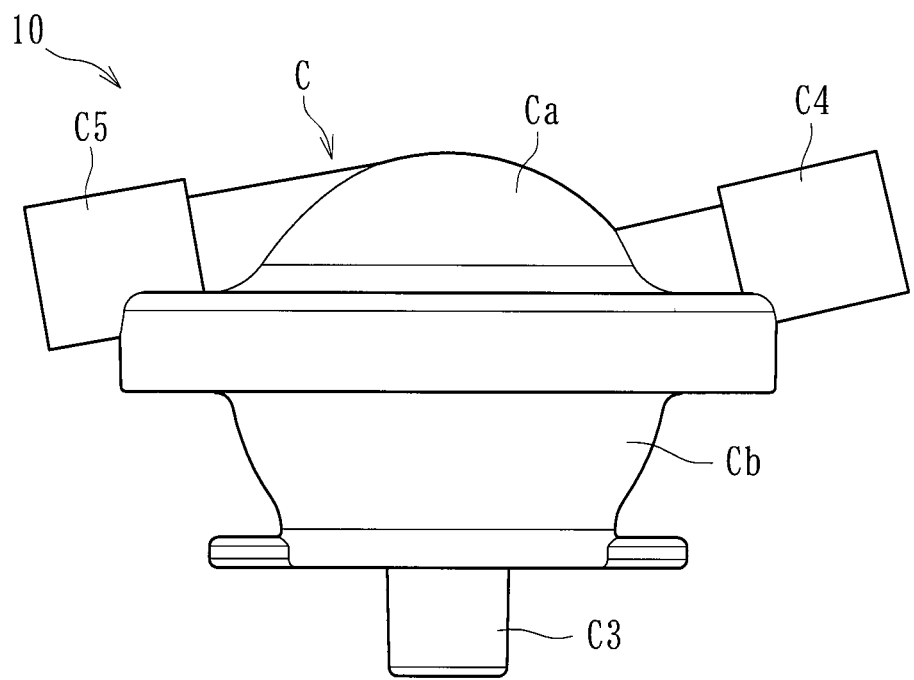

[Fig. 14]
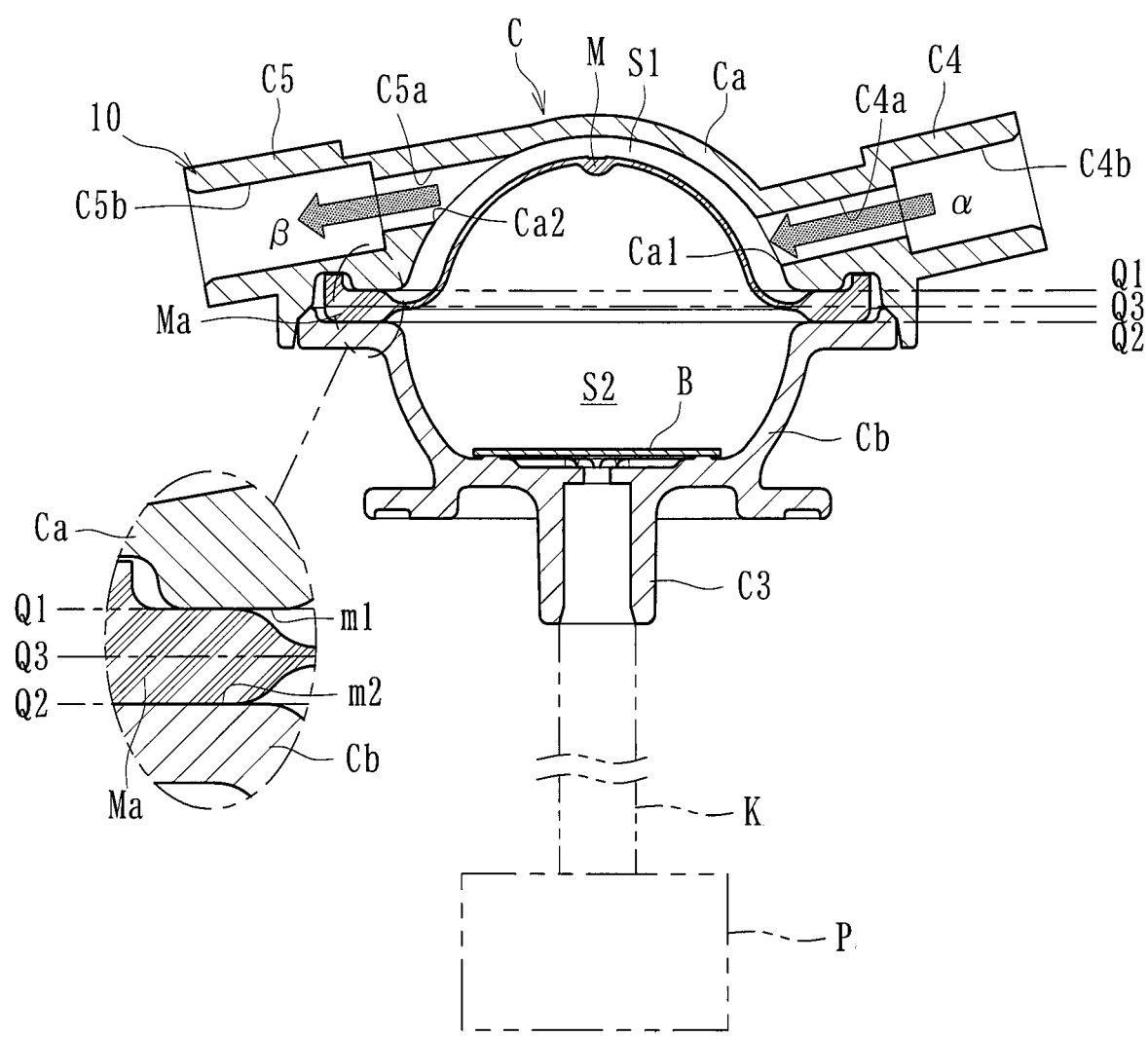

[ Fig. 15 ]
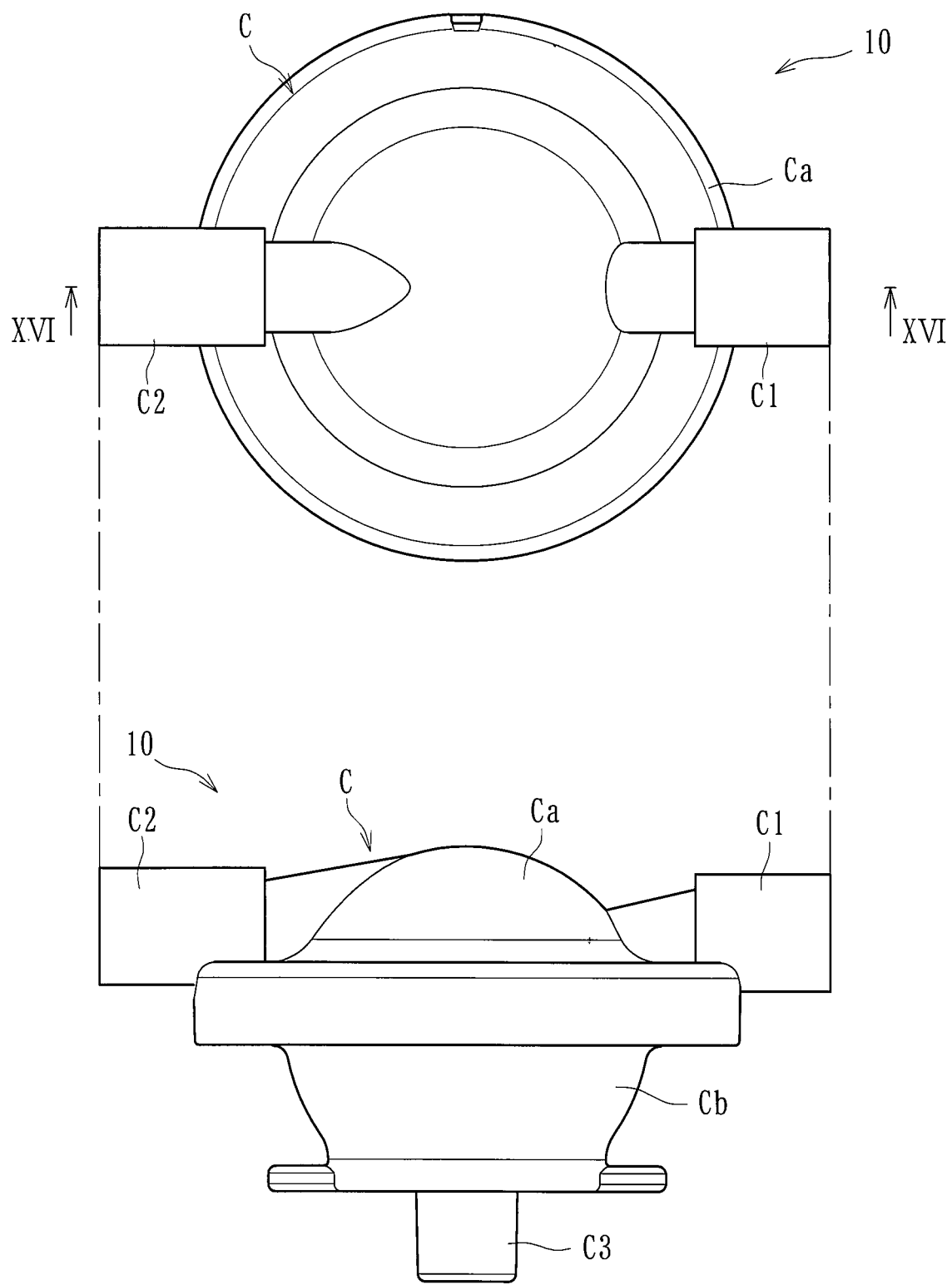

[ Fig. 16 ]
(a)
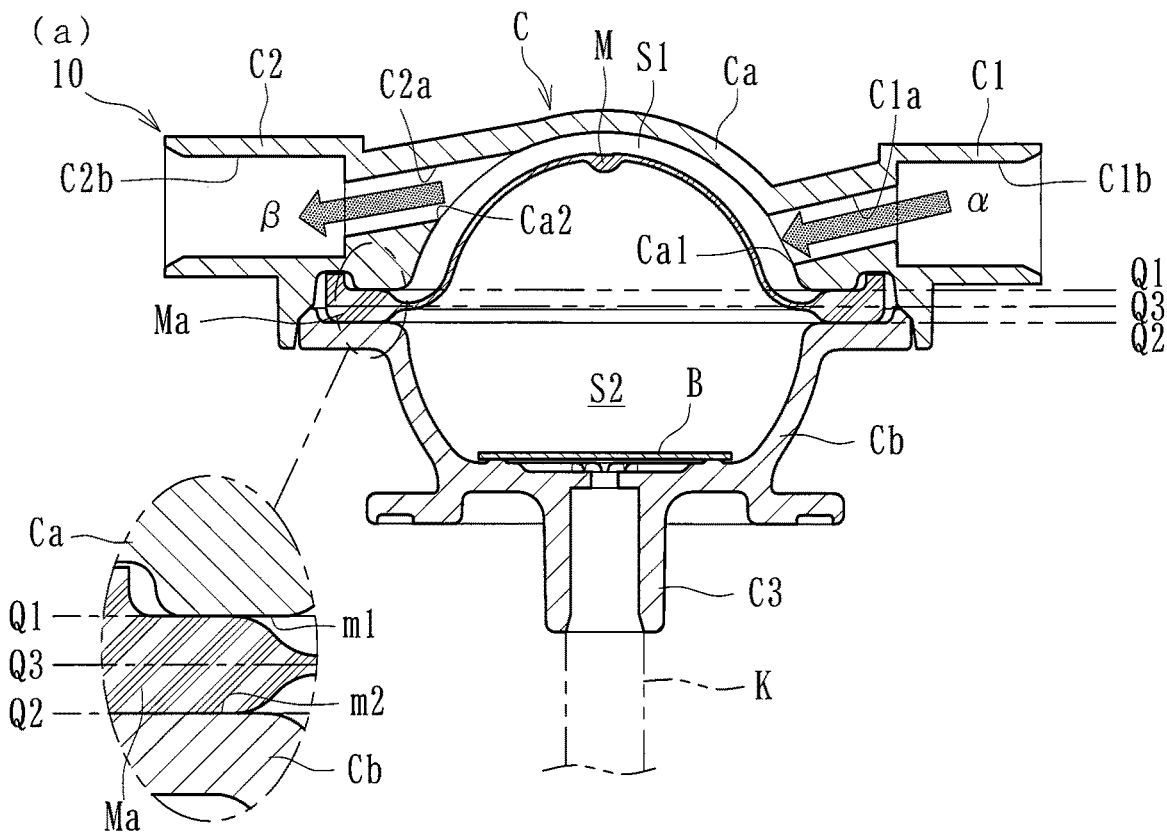
(b)
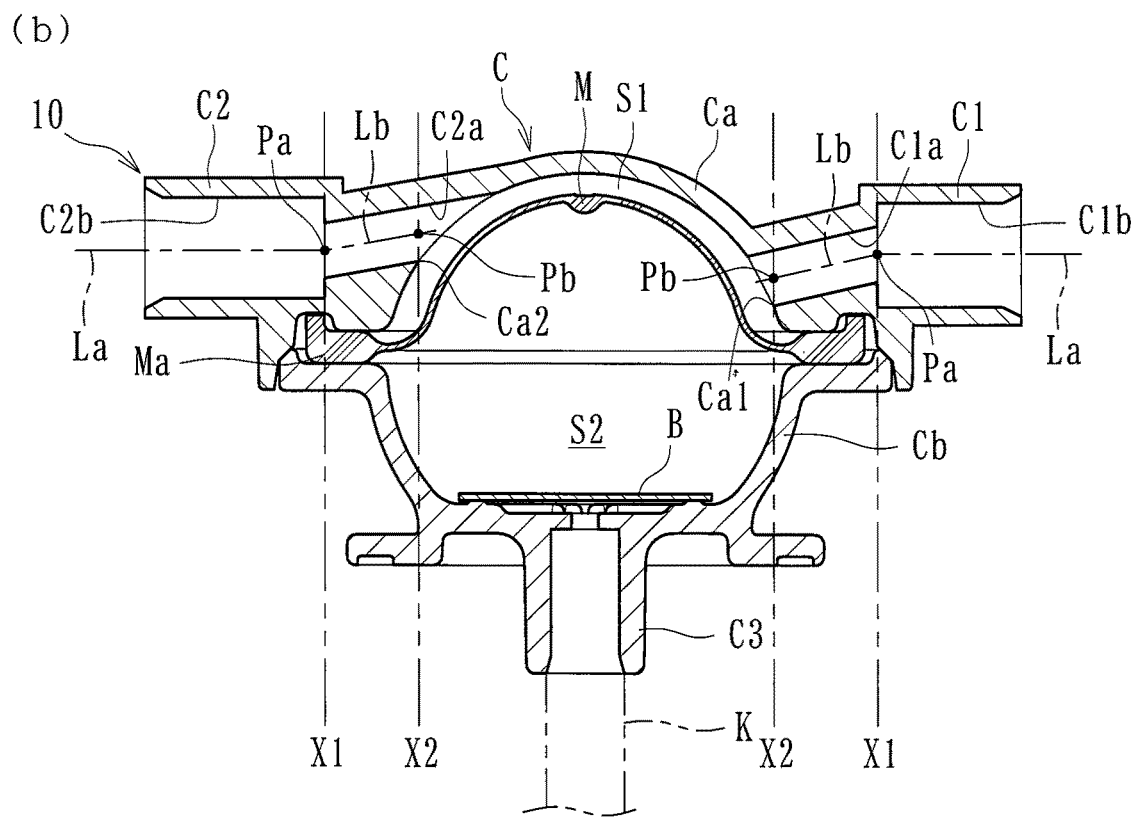

[Fig. 17]
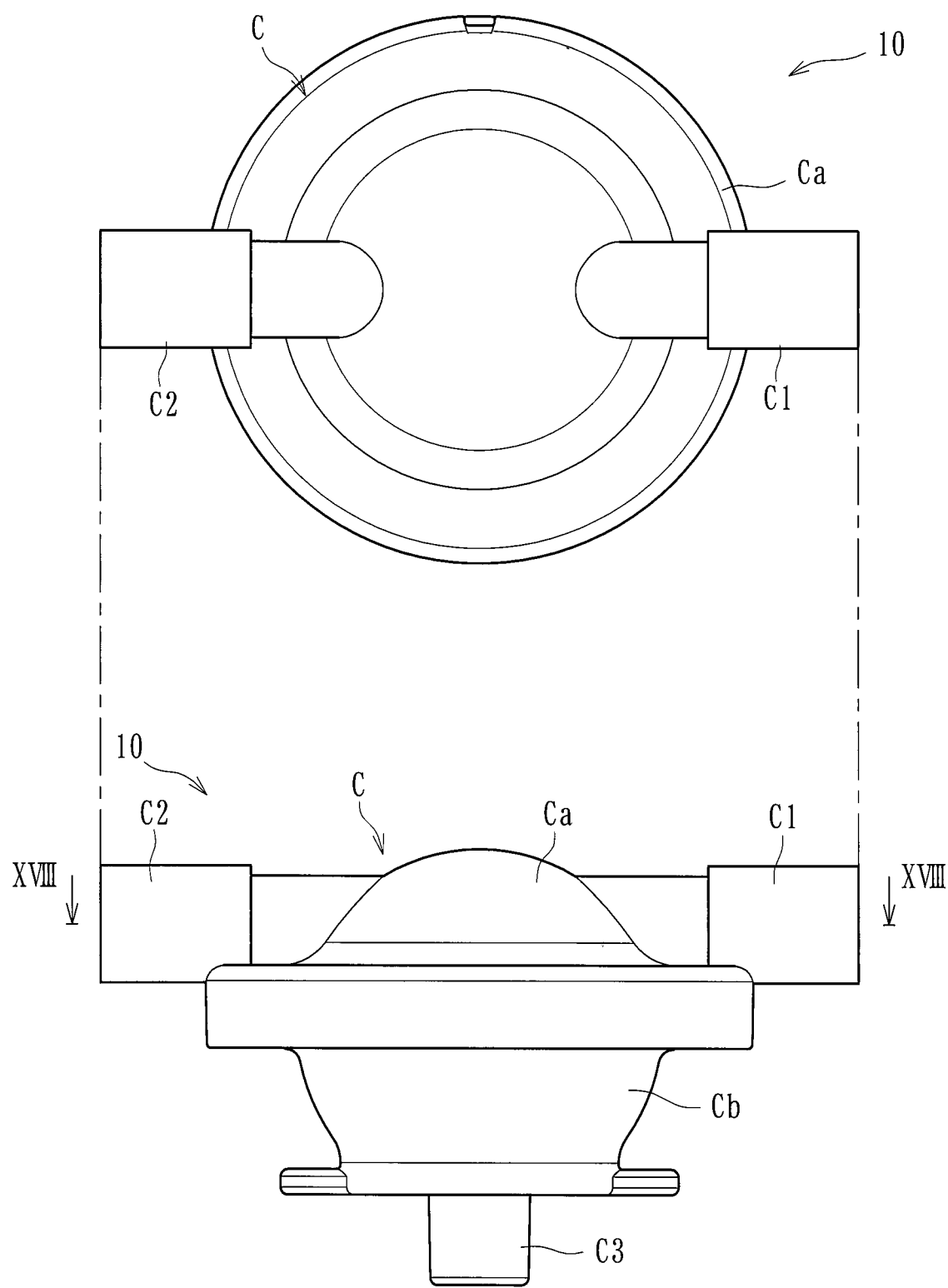

[ Fig. 18 ]
(a)
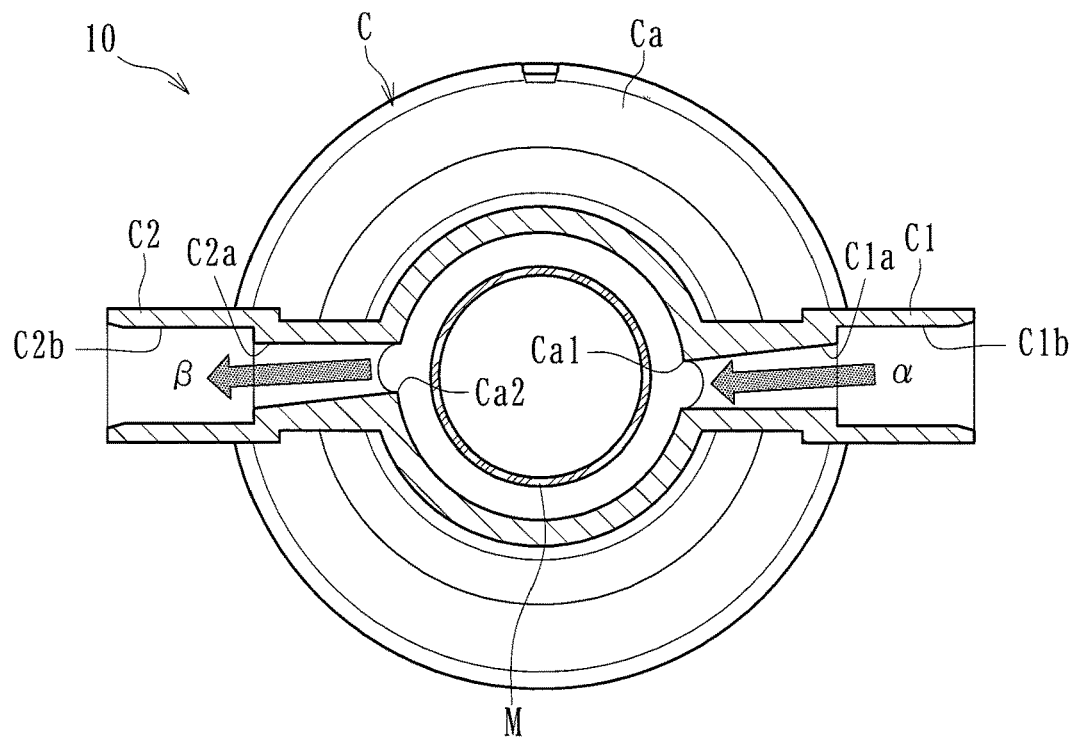
(b)
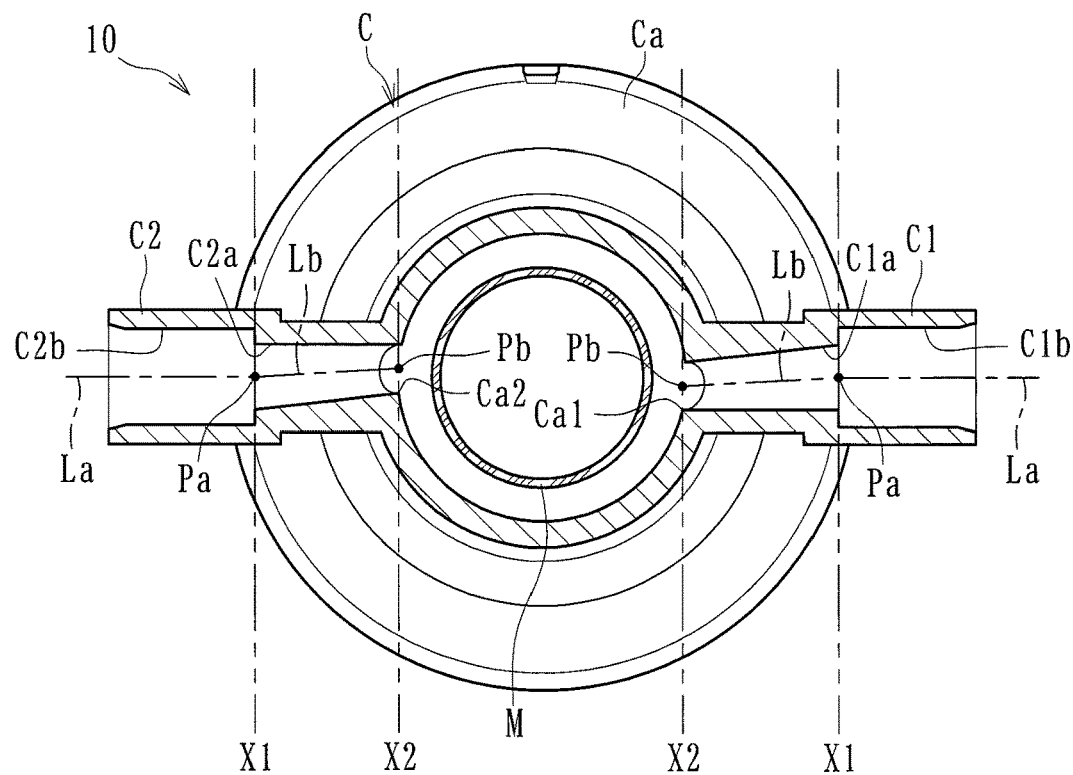

[ Fig. 19 ]
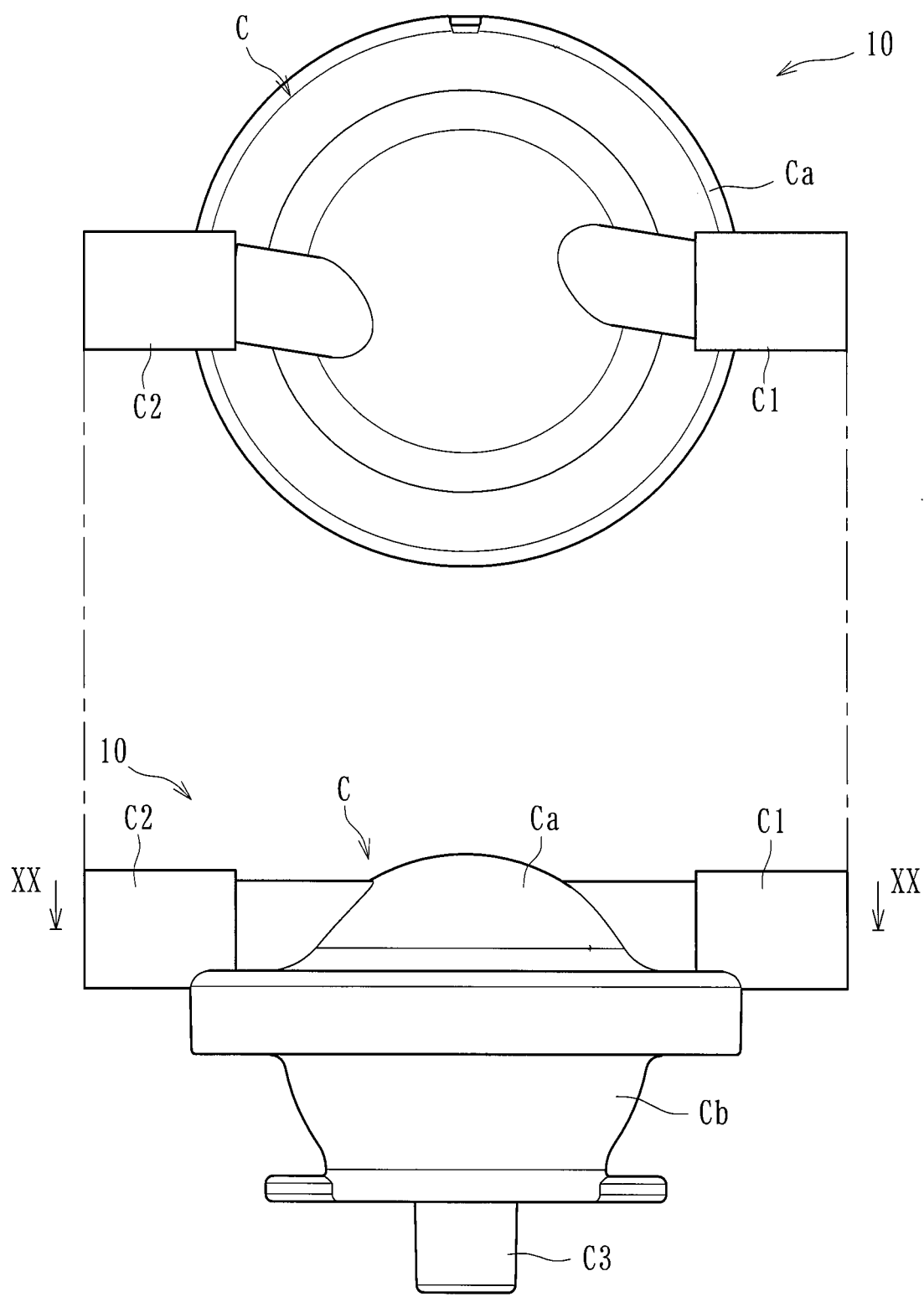

[Fig. 20]
(a)
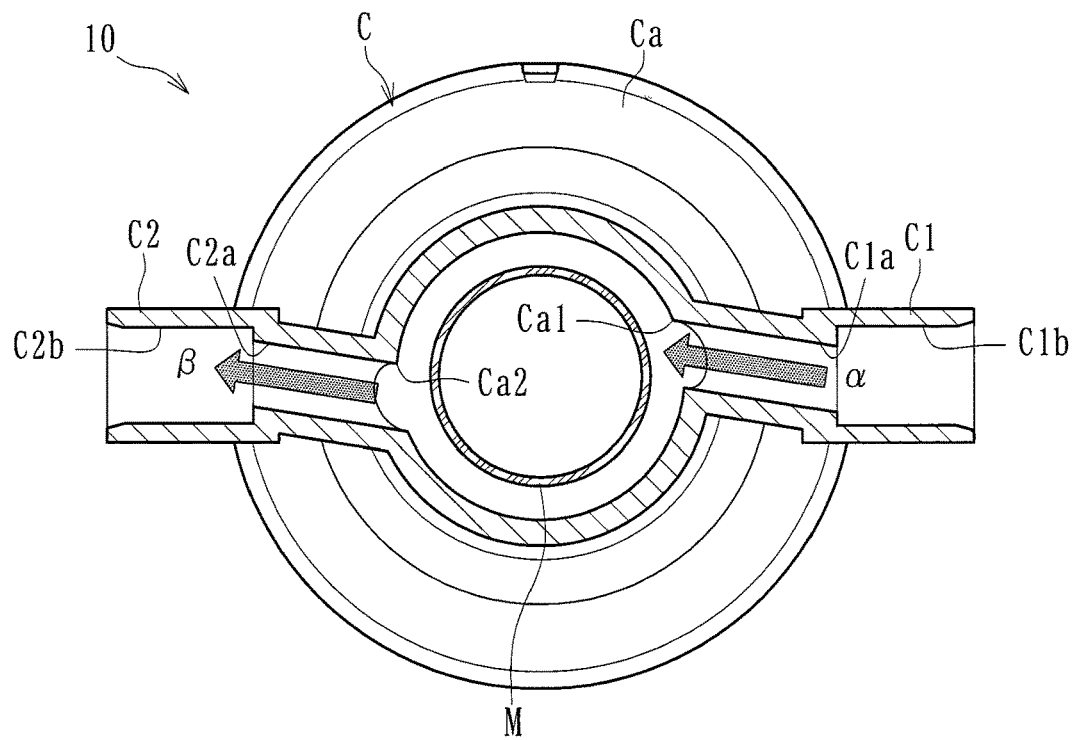
(b)
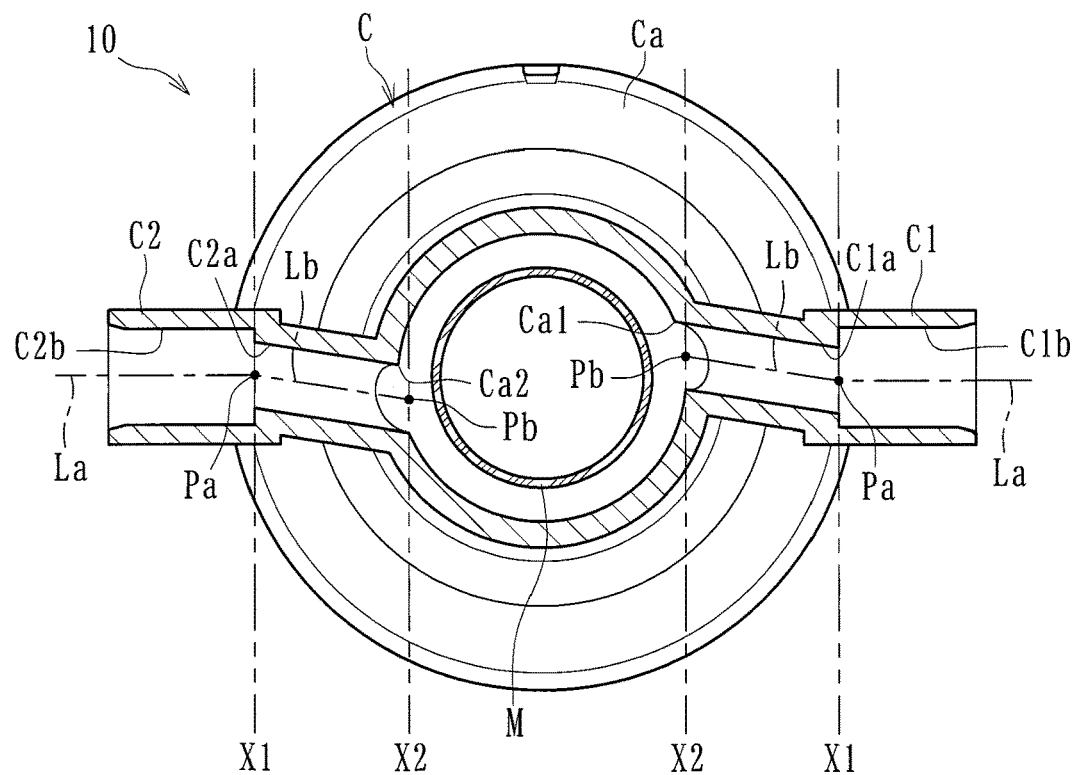

PRESSURE DETECTOR

CROSS-REFERENCE TO RELATED APPLICATION(S)

This application is a continuation of International Application No. PCT/JP2019/019393, filed on May 15, 2019, which claims priority to Japanese Application No. 2018-094462, filed on May 16, 2018, the entire disclosures of which are hereby incorporated by reference.

FIELD

The present invention relates to a pressure detector capable of detecting the pressure of liquid in a flow route by detecting the pressure in a gas-phase portion.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and (a) venous puncture needle, respectively. The patient is punctured with the puncture needles, and extracorporeal circulation of blood in the dialysis treatment is thus performed.

To detect the pressure of blood that extracorporeally circulates through a blood circuit, a pressure detector has been proposed as disclosed by PTL 1, for example. The pressure detector includes a case connectable to a blood circuit, and a diaphragm (a membrane member) attached inside the case and with which a liquid-phase portion to be supplied with blood in the blood circuit and a gas-phase portion to be supplied with air are separated from each other, the diaphragm being displaceable in accordance with the pressure of the blood supplied to the liquid-phase portion, the pressure detector being capable of detecting the pressure of the blood by detecting the pressure in the gas-phase portion with a pressure detection sensor. With such a known pressure detector, since the liquid-phase portion and the gas-phase portion are separated from each other by the membrane member, the pressure of the blood in the blood circuit can be detected accurately while the blood is prevented from coming into contact with the air in the gas-phase portion.

To suppress blood retention in the liquid-phase portion of such a pressure detector, there is another known proposal in which an inlet port that allows blood to flow into the liquid-phase portion and an outlet port that allows the blood having flowed into the liquid-phase portion to be discharged are offset from each other, so that an inlet opening and an outlet opening do not face each other (see PTL 2, for example). In such a pressure detector, the blood having flowed thereinto through the inlet opening is stirred in the liquid-phase portion and is then discharged therefrom through the outlet opening. Therefore, blood retention in the liquid-phase portion can be suppressed.

PTL 1: Japanese Unexamined Patent Application Publication (Translation of PCT Application) No. 2017-504389 and PTL 2: Japanese Unexamined Patent Application Publication No. 2008-136673 the teachings of which are expressly incorporated by reference herein for all purposes.

SUMMARY

However, in the above known pressure detector, which has a round columnar shape, the axes of the inlet port and the outlet port are parallel to each other and offset from each other. Therefore, the capacity of the liquid-phase portion tends to be large. Consequently, the volume of priming to be performed with the pressure detector connected to the blood circuit tends to be large. Moreover, it is difficult to produce a satisfactory effect of stirring in the liquid-phase portion.

The present invention has been conceived in view of the above circumstances and provides a pressure detector in which liquid in a liquid-phase portion can be stirred satisfactorily while the increase in the capacity of the liquid-phase portion is suppressed.

Variation 1 may comprise a pressure detector that includes a case connectable to a flow route for liquid, and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The pressure detector includes an inlet port including a connecting portion connectable to the flow route for the liquid, and a flow-route portion through which the liquid flows into an inlet opening of the liquid-phase portion; and an outlet port including a connecting portion connectable to the flow route for the liquid, and a flow-route portion through which the liquid having flowed into the liquid-phase portion is discharged from an outlet opening. At least one of the flow-route portion of the inlet port and the flow-route portion of the outlet port is configured such that an incoming direction or an outgoing direction of the liquid is inclined with respect to an attaching plane defined for the membrane member.

Variation 2 according to the pressure detector of variation 1, where at least the flow-route portion of the inlet port has a diameter gradually reduced toward the liquid-phase portion.

Variation 3 according to the pressure detector of variation 1 or 2, where the inlet port and the outlet port form a predetermined angle with respect to each other in a circumferential direction of the case.

Variation 4 according to the pressure detector of variations 1 to 3, where the flow-route portion of the inlet port and the flow-route portion of the outlet port are configured such that the incoming direction and the outgoing direction of the liquid are offset from each other.

Variation 5 according to the pressure detector of variations 1 to 4, where the case includes a liquid-phase-portion case defining the liquid-phase portion, and a gas-phase-portion case defining the gas-phase portion; and the attaching plane defined for the membrane member is a virtual plane containing a holding surface where the membrane member is held between the liquid-phase-portion case and the gas-phase-portion case that are mated to each other.

Variation 6 according to the pressure detector of variations 1 to 5, where at least one of the inlet port and the outlet port is configured such that a virtual line connecting a first center point as a center position of the flow-route portion in a boundary plane defined between the flow-route portion and the connecting portion and a second center point as a center position of the flow-route portion in a plane extending parallel to the boundary plane and containing an opening edge of the inlet opening or the outlet opening is inclined with respect to a center line of the connecting portion.

Variation 7 may comprise a pressure detector that includes a case connectable to a flow route for liquid, and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion. The pressure detector includes an inlet port including a connecting portion connectable to the flow route for the liquid, and a flow-route portion through which the liquid flows into an inlet opening of the liquid-phase portion; and an outlet port including a connecting portion connectable to the flow route for the liquid, and a flow-route portion through which the liquid having flowed into the liquid-phase portion is discharged from an outlet opening. The flow-route portion of the inlet port or the flow-route portion of the outlet port is configured such that an incoming direction or an outgoing direction of the liquid is parallel to an attaching plane defined for the membrane member, and such that an extension of a virtual line connecting a first center point as a center position of the flow-route portion in a boundary plane defined between the flow-route portion and the connecting portion of one of the inlet port and the outlet port and a second center point as a center position of the flow-route portion in a plane extending parallel to the boundary plane and containing an opening edge of the inlet opening or the outlet opening does not pass through the second center point of an other of the inlet port and the outlet port.

Variation 8 according to the pressure detector of variation 7, where at least the flow-route portion of the inlet port has a diameter gradually reduced toward the liquid-phase portion.

Variation 9 according to the pressure detector of variations 7 or 8, the inlet port and the outlet port form a predetermined angle with respect to each other in a circumferential direction of the case.

Variation 10 according to the pressure detector of variations 7 to 9, the flow-route portion of the inlet port and the flow-route portion of the outlet port are configured such that the incoming direction and the outgoing direction of the liquid are offset from each other.

Variation 11 according to the pressure detector of variations 7 to 10, the case includes a liquid-phase-portion case defining the liquid-phase portion, and a gas-phase-portion case defining the gas-phase portion; and the attaching plane defined for the membrane member is a virtual plane containing a holding surface where the membrane member is held between the liquid-phase-portion case and the gas-phase-portion case that are mated to each other.

Variation 12 according to the pressure detector of variations 7 to 11, the virtual line connecting the first center point and the second center point is inclined with respect to a center line of the connecting portion.

Variation 13 may comprise a blood circuit to which the pressure detector according to any of variations 1 to 12 is connected.

According to variation 14, at least one of the flow-route portion of the inlet port and the flow-route portion of the outlet port is configured such that the incoming direction or the outgoing direction of the liquid is inclined with respect to the attaching plane defined for the membrane member. Therefore, while the increase in the capacity of the liquid-phase portion is suppressed, the liquid in the liquid-phase portion can be stirred satisfactorily.

According to variation 15, at least the flow-route portion of the inlet port has a diameter gradually reduced toward the liquid-phase portion. Therefore, the flow velocity of the liquid flowing into the liquid-phase portion is increased. Thus, retention in the liquid-phase portion can be suppressed assuredly.

According to variation 16, the inlet port and the outlet port form the predetermined angle with respect to each other in the circumferential direction of the case. Therefore, while the increase in the capacity of the liquid-phase portion is suppressed further, the inlet opening and the outlet opening can be prevented from facing each other. Thus, the effect of stirring the liquid in the liquid-phase portion can be increased further.

According to variation 17, the flow-route portion of the inlet port and the flow-route portion of the outlet port are configured such that the incoming direction and the outgoing direction of the liquid are offset from each other. Therefore, while the increase in the capacity of the liquid-phase portion is suppressed further, the effect of stirring the liquid in the liquid-phase portion can be increased further.

According to variation 18, the case includes the liquid-phase-portion case defining the liquid-phase portion, and the gas-phase-portion case defining the gas-phase portion. Furthermore, the attaching plane defined for the membrane member is the virtual plane containing the holding surface where the membrane member is held between the liquid-phase-portion case and the gas-phase-portion case that are mated to each other. Therefore, the inlet port or the outlet port can be made accurately inclined with respect to the attaching plane.

According to variation 19, at least one of the inlet port and the outlet port is configured such that the virtual line connecting the first center point as the center position of the flow-route portion in the boundary plane defined between the flow-route portion and the connecting portion and the second center point as the center position of the flow-route portion in the plane extending parallel to the boundary plane and containing the opening edge of the inlet opening or the outlet opening is inclined with respect to the center line of the connecting portion. Therefore, the effect of stirring the liquid in the liquid-phase portion can be increased further.

According to variation 20, the flow-route portion of the inlet port or the flow-route portion of the outlet port is configured such that the incoming direction or the outgoing direction of the liquid is parallel to the attaching plane defined for the membrane member, and such that the extension of the virtual line connecting the first center point as the center position of the flow-route portion in the boundary plane defined between the flow-route portion and the connecting portion of one of the inlet port and the outlet port and the second center point $Pb$ as the center position of the flow-route portion in the plane extending parallel to the boundary plane and containing the opening edge of the inlet opening or the outlet opening does not pass through the second center point of the other of the inlet port and the outlet port. Therefore, while the increase in the capacity of the liquid-phase portion is suppressed, the liquid in the liquid-phase portion can be stirred satisfactorily.

According to variation 21, at least the flow-route portion of the inlet port has a diameter gradually reduced toward the liquid-phase portion. Therefore, the flow velocity of the liquid flowing into the liquid-phase portion is increased. Thus, retention in the liquid-phase portion can be suppressed assuredly.

According to variation 22, the inlet port and the outlet port form the predetermined angle with respect to each other in the circumferential direction of the case. Therefore, while the increase in the capacity of the liquid-phase portion is suppressed further, the inlet opening and the outlet opening can be prevented from facing each other. Thus, the effect of stirring the liquid in the liquid-phase portion can be increased further.

According to variation 23, the flow-route portion of the inlet port and the flow-route portion of the outlet port are configured such that the incoming direction and the outgoing direction of the liquid are offset from each other. Therefore, while the increase in the capacity of the liquid-phase portion is suppressed further, the effect of stirring the liquid in the liquid-phase portion can be increased further.

According to variation 24, the case includes the liquid-phase-portion case defining the liquid-phase portion, and the gas-phase-portion case defining the gas-phase portion. Furthermore, the attaching plane defined for the membrane member is the virtual plane containing the holding surface where the membrane member is held between the liquid-phase-portion case and the gas-phase-portion case that are mated to each other. Therefore, the inlet port or the outlet port can be made accurately inclined with respect to the attaching plane.

According to variation 25, the virtual line connecting the first center point and the second center point is inclined with respect to the center line of the connecting portion. Therefore, the effect of stirring the liquid in the liquid-phase portion can be increased further.

According to variation 26, a blood circuit producing the above advantageous effects of the pressure detector according to any of variations 1 to 12 can be provided.

BRIEF DESCRIPTION OF THE DRAWINGS

FIG. 1 is a schematic diagram illustrating a dialysis apparatus (a blood purification apparatus) to which a pressure detector according to a first embodiment of the present invention is applied.

FIG. 2 is a plan view of the pressure detector.

FIG. 3 is a front view of the pressure detector.

FIG. 4 is a sectional view taken along line IV-IV illustrated in FIG. 2.

FIG. 5 is a sectional view taken along line V-V illustrated in FIG. 2 (with a membrane member displaced toward the side of a liquid-phase portion).

FIG. 6 is a sectional view taken along line V-V illustrated in FIG. 2 (with the membrane member displaced toward the side of a gas-phase portion).

FIG. 7 is a plan view of an inlet opening and an outlet opening provided in a liquid-phase-portion case included in the pressure detector.

FIG. 8 is a plan view of a gas-phase-portion case included in the pressure detector (with a hydrophobic membrane yet to be attached thereto).

FIG. 9 is a plan view of the gas-phase-portion case included in the pressure detector (with the hydrophobic membrane attached thereto).

FIG. 10 is a sectional view of part of the pressure detector where the hydrophobic membrane is attached.

FIG. 11 includes sectional views of the pressure detector and each illustrate a flow-route portion of an inlet port and a flow-route portion of an outlet port.

FIG. 12 is a plan view of a pressure detector according to a second embodiment of the present invention.

FIG. 13 is a front view of the pressure detector.

FIG. 14 is a sectional view taken along line XIV-XIV illustrated in FIG. 12.

FIG. 15 includes a plan view and a front view of a pressure detector according to a third embodiment of the present invention.

FIG. 16 includes sectional views taken along line XVI-XVI illustrated in FIG. 15.

FIG. 17 includes a plan view and a front view of a pressure detector according to a fourth embodiment of the present invention.

FIG. 18 includes sectional views taken along line XVIII-XVIII illustrated in FIG. 17.

FIG. 19 includes a plan view and a front view of a pressure detector according to a fifth embodiment of the present invention.

FIG. 20 includes sectional views taken along line XX-XX illustrated in FIG. 19.

DETAILED DESCRIPTION

Embodiments of the present invention will now be described specifically with reference to the drawings.

A blood purification apparatus applied to a first embodiment is a dialysis apparatus for giving dialysis treatment and basically includes, as illustrated in FIG. 1, a blood circuit including an arterial blood circuit 1 and a venous blood circuit 2, a dialyzer 3 (a blood purifier) provided between the arterial blood circuit 1 and the venous blood circuit 2 and that purifies blood flowing through the blood circuit, a blood pump 4, an air-trap chamber 5 provided to the venous blood circuit 2, a dialysis device 6 that supplies dialysate to the dialyzer 3 and drains waste liquid from the dialyzer 3, a physiological-saline supply line L3 (a substitution-fluid supply line) that allows physiological saline as a substitution fluid to be supplied to the blood circuit, and a storage unit 7 that stores the physiological saline as the substitution fluid.

The arterial blood circuit 1 is provided with an arterial puncture needle (a) connectable to a distal end thereof through a connector, and the blood pump 4, which is of a peristaltic type, at a halfway position thereof. The venous blood circuit 2 is provided with a venous puncture needle (b) connectable to a distal end thereof through a connector, and the air-trap chamber 5 at a halfway position thereof. The air-trap chamber 5 is capable of trapping bubbles in the liquid and is provided with a filtering net (not illustrated), thereby being capable of trapping, for example, thrombi and the like at the time of blood return. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The blood pump 4, which is a peristaltic pump provided to the arterial blood circuit 1, is capable of undergoing normal rotation and reverse rotation and causing the liquid in the blood circuit to flow in the direction of rotation thereof. Specifically, the arterial blood circuit 1 includes a squeezable tube that is softer and has a larger diameter than other flexible tubes forming the arterial blood circuit 1. The blood pump 4 includes rollers for squeezing the squeezable tube in the direction of liquid delivery. When the blood pump 4 is activated, the rollers rotate and thus squeeze the squeezable tube (a portion of the blood circuit), whereby the liquid in the tube can be made to flow in the direction of rotation (the direction in which the rollers rotate).

When the blood pump 4 is activated to undergo normal rotation (leftward rotation in the drawing) while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, the patient's blood is purified with the dialyzer 3 while being caused to extracorporeally circulate through the blood circuit from the distal end of the arterial blood circuit 1 to the distal end of the venous blood circuit 2. When the blood pump 4 is activated to undergo reverse rotation (rightward rotation in the drawing), the blood in the blood circuit (a portion of the arterial blood circuit 1 that is between the distal end and a position where the blood pump 4 is provided) can be returned to the patient.

The dialyzer 3 has, in a housing thereof, a blood introduction port 3a, a blood delivery port 3b, a dialysate introduction port 3c, and a dialysate delivery port 3d. The blood introduction port 3a is connected to the arterial blood circuit 1. The blood delivery port 3b is connected to the venous blood circuit 2. The dialysate introduction port 3c and the dialysate delivery port 3d are connected to a dialysate introduction line L1 and a dialysate drain line L2, respectively, extending from the dialysis device 6.

The dialyzer 3 houses a plurality of hollow fibers. Spaces inside the respective hollow fibers form flow routes for blood, and spaces between the inner surface of the housing and the outer surfaces of the hollow fibers form flow routes for dialysate. The hollow fibers each have a number of microscopic holes (pores) extending therethrough from the outer surface to the inner surface, thereby forming a hollow fiber membrane. Impurities and the like contained in the blood are allowed to permeate through the hollow fiber membranes into the dialysate.

On the other hand, the dialysis device 6 includes a liquid delivery unit such as a duplex pump provided over the dialysate introduction line L1 and the dialysate drain line L2. A bypass line that bypasses the liquid delivery unit is provided with an ultrafiltration pump for removing water from the patient's blood flowing in the dialyzer 3. One end of the dialysate introduction line L1 is connected to the dialyzer 3 (the dialysate introduction port 3c), and the other end is connected to a dialysate supply device (not illustrated) that prepares a dialysate at a predetermined concentration. One end of the dialysate drain line L2 is connected to the dialyzer 3 (the dialysate delivery port 3d), and the other end is connected to a drainage unit, not illustrated. The dialysate supplied from the dialysate supply device flows through the dialysate introduction line L1 into the dialyzer 3, and further flows through the dialysate drain line L2 into the drainage unit.

The air-trap chamber 5 is provided with an overflow line extending from the top thereof. The overflow line is provided with a clamp unit, such as an electromagnetic valve, at a halfway position thereof. When the clamp unit such as an electromagnetic valve is opened, the liquid (a priming solution or the like) flowing in the blood circuit can be made to overflow through the overflow line.

The physiological-saline supply line L3 (the substitution-fluid supply line) is connected at one end thereof to the arterial blood circuit 1 between the position where the blood pump 4 is provided and the distal end of the arterial blood circuit 1 through a T-shaped pipe or the like. The physiological-saline supply line L3 forms a flow route (such as a flexible tube or the like) through which the physiological saline (the substitution fluid) to substitute for the blood in the blood circuit is allowed to be supplied to the arterial blood circuit 1. The physiological-saline supply line L3 is provided at the other end thereof with the storage unit 7 (a so-called "saline bag"), in which a predetermined amount of physiological saline is stored. The physiological-saline supply line L3 is further provided at a halfway position thereof with an air-trap chamber 8.

The physiological-saline supply line L3 according to the present embodiment is further provided with a clamp unit 9 (such as an electromagnetic valve or the like). The clamp unit 9 is capable of opening and closing the physiological-saline supply line L3, thereby closing and opening the flow route. The state of the physiological-saline supply line L3 is arbitrarily switchable by opening or closing the clamp unit 9, between a closed state where the flow route is closed and an open state where the physiological saline (substitution fluid) is allowed to flow. The clamp unit 9 may be replaced with a general-purpose device such as a pair of forceps with which the flow route of the physiological-saline supply line L3 can be manually closed and opened.

The blood circuit applied to the present embodiment is provided with a pressure detector 10. The pressure detector 10 is connected to the venous blood circuit 2 at a position between the dialyzer 3 and the air-trap chamber 5 and is capable of detecting the pressure of the blood flowing in the venous blood circuit 2 (the blood circuit). Specifically, as illustrated in FIGS. 2 to 6, the pressure detector 10 includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P.

The case C is a hollow molded component obtained by molding a predetermined resin material or the like. The case C is a combination of a liquid-phase-portion case Ca defining the liquid-phase portion S1 and a gas-phase-portion case Cb defining the gas-phase portion S2. The liquid-phase-portion case Ca has an inlet port C1 and an outlet port C2 integrally molded therewith. The inlet port C1 and the outlet port C2 are each connectable to the flow route for liquid and allow the flow route to communicate with the liquid-phase portion S1. The gas-phase-portion case Cb has a connection port C3 integrally molded therewith. The connection port C3 is connectable to one end of the pipe K, to be described below, and allows the one end to communicate with the gas-phase portion S2. The functions of the inlet port C1 and the outlet port C2 of introducing and discharging the liquid may be switched therebetween (that is, the liquid may be discharged from the inlet port C1 while being introduced into the outlet port C2).

The liquid-phase-portion case Ca has an annular holding surface m1 (see FIG. 7) at the periphery thereof. The gas-phase-portion case Cb has an annular holding surface m2 (see FIGS. 8 and 9) at the periphery thereof. When the liquid-phase-portion case Ca and the gas-phase-portion case Cb are mated to each other, a rim Ma of the membrane member M is placed between the holding surface m1 and the holding surface m2. Thus, the membrane member M can be attached in a sealing manner. A space thus provided in the case C is separated (sectioned) by the membrane member M into the liquid-phase portion S1 and the gas-phase portion S2.

The membrane member M serves as a diaphragm provided in the case C and is made of a flexible material that is displaceable or deformable in conformity with pressure change occurring in the liquid-phase portion S1 or the gas-phase portion S2. Specifically, if the pressure of the liquid (the hydraulic pressure) in the liquid-phase portion S1 is low, as illustrated in FIG. 5, the membrane member M is displaced toward the side of the liquid-phase portion S1, whereby the capacity of the gas-phase portion S2 is increased. If the pressure of the liquid (the hydraulic pressure) in the liquid-phase portion S1 is high, as illustrated in FIG. 6, the membrane member M is displaced toward the side of the gas-phase portion S2, whereby the capacity of the gas-phase portion S2 is reduced.

The gas-phase-portion case Cb has an opening Cb1 (see FIG. 8) substantially at the center of the bottom thereof. The opening Cb1 provided in the inner surface (the bottom) of the gas-phase-portion case Cb allows the flow route in the connection port C3 and the gas-phase portion S2 to communicate with each other. Accordingly, air (gas) is to be introduced into or discharged from the gas-phase portion S2 in accordance with the displacement of the membrane member M. The pipe K is connected at one end thereof to the connection port C3 and at the other end thereof to the pressure detection sensor P. Therefore, as air (gas) is introduced or discharged through the opening Cb1 with the displacement of the membrane member M, the pressure detection sensor P can detect the pressure in the gas-phase portion S2. Note that the connection port C3 is not limited to the one to be connected to the pipe K and may be connected to another element capable of transmitting the pressure in the gas-phase portion S2 to the pressure sensor P.

The gas-phase-portion case Cb according to the present embodiment has recesses Cb4 surrounding the opening Cb1 provided at the bottom thereof. Furthermore, as illustrated in FIGS. 8 to 10, the gas-phase-portion case Cb is provided with a hydrophobic membrane B that covers the recesses Cb4, inclusive of the opening Cb1. The hydrophobic membrane B is a member formed as a membrane that allows gas to pass therethrough but blocks liquid from passing therethrough. The periphery of the hydrophobic membrane B is welded (for example, by ultrasonic welding or the like) to a ridge Cb3 provided around the opening Cb1.

As illustrated in FIG. 8, the recesses Cb4 are defined by a plurality of ribs Cb2 projecting radially about the opening Cb1, so that the bending of the hydrophobic membrane B toward the opening Cb1 can be limited. Specifically, when the hydrophobic membrane B bends toward the opening Cb1 (toward the recesses Cb4), the hydrophobic membrane B comes into contact with the ribs Cb2, thereby being prevented from bending further. Hence, spaces around the opening Cb1 (spaces in the recesses Cb4) can be preserved. Accordingly, the opening Cb1 can be prevented from being closed at the displacement of the membrane member M.

The inlet port C1 according to the present embodiment is a portion (a projected portion) connectable to the flow route for liquid (the blood circuit) and includes, as illustrated in FIGS. 4 and 11, a flow-route portion C1a through which the liquid (blood) flows into an inlet opening Ca1 (see FIG. 7) of the liquid-phase portion S1, and a connecting portion C1b connectable to the flow route (the blood circuit). Specifically, the flow-route portion C1a and the connecting portion C1b are continuous with each other in the axial direction thereof in the projected portion forming the inlet port C1. When a tube forming the flow route is connected to the connecting portion C1b, the liquid in the flow route can be made to flow into the flow-route portion C1a and then into the liquid-phase portion S1 through the inlet opening Ca1. Note that the inlet port C1 may be shaped as a recess to which the tube forming the flow route is to be connected.

The outlet port C2 according to the present embodiment is a portion (a projected portion) connectable to the flow route for liquid (the blood circuit) and includes, as illustrated in the drawings, a flow-route portion C2a through which the liquid (blood) having flowed into the liquid-phase portion S1 is discharged from an outlet opening Ca2 (see FIG. 7), and a connecting portion C2b connectable to the flow route (the blood circuit). Specifically, the flow-route portion C2a and the connecting portion C2b are continuous with each other in the axial direction thereof in the projected portion forming the outlet port C2. When a tube forming the flow route is connected to the connecting portion C2b, the liquid having flowed into the liquid-phase portion S1 can be made to flow into the flow-route portion C2a and then to be discharged to a flow route (the blood circuit) on the downstream side. Note that the outlet port C2 may be shaped as a recess to which the tube forming the flow route is to be connected.

As illustrated in FIG. 11, the flow-route portion C1a of the inlet port C1 and the flow-route portion C2a of the outlet port C2 according to the present embodiment are set such that an incoming direction $\alpha$ and an outgoing direction $\beta$ of the liquid are inclined with respect to an attaching plane Q defined for the membrane member M. Specifically, the attaching plane Q according to the present embodiment is a virtual plane containing the holding surface m1 that holds the membrane member M. With reference to the attaching plane Q, the flow-route portion C1a of the inlet port C1 allows the liquid to flow in a direction (the incoming direction $\alpha$) inclined downward from the connecting portion C1b toward the liquid-phase portion S1, and the flow-route portion C2a of the outlet port C2 allows the liquid to be discharged in a direction (the outgoing direction $\beta$) inclined downward from the liquid-phase portion S1 toward the connecting portion C2b.

In the present embodiment, the flow-route portion C1a of the inlet port C1 and the flow-route portion C2a of the outlet port C2 are configured such that the incoming direction $\alpha$ and the outgoing direction $\beta$ of the liquid are inclined with respect to the attaching plane Q defined for the membrane member M. Note that at least one of the flow-route portion C1a of the inlet port C1 and the flow-route portion C2a of the outlet port C2 only needs to be configured such that the incoming direction $\alpha$ or the outgoing direction $\beta$ of the liquid is inclined with respect to the attaching plane Q defined for the membrane member M.

The attaching plane Q defined for the membrane member M is the reference for inclining the incoming direction $\alpha$ or the outgoing direction $\beta$ of the liquid. As illustrated in FIGS. 5 and 6, the attaching plane Q, which is the virtual plane Q1 containing the holding surface m1 of the liquid-phase-portion case Ca in the above case, may be a virtual plane Q2 containing the holding surface m2 of the gas-phase-portion case Cb, or a virtual plane Q3 containing a plane extending along the height-direction center of the rim Ma of the membrane member M. That is, in the present invention, the incoming direction α or the outgoing direction β of the liquid is inclined with respect to the attaching plane Q, which is any of the attaching plane Q1 containing the holding surface m1 of the liquid-phase-portion case Ca, the attaching plane Q2 containing the holding surface m2 of the gas-phase-portion case Cb, and the attaching plane Q3 containing the plane extending along the height-direction center of the rim Ma of the membrane member M.

As illustrated in FIG. 2, the inlet port C1 and the outlet port C2 according to the present embodiment project in such a manner as to form a predetermined angle f with respect to each other in the circumferential direction of the case C. The liquid-phase-portion case Ca has a connecting recess Ca3 (see FIG. 7) provided between the inlet opening Ca1 and the outlet opening Ca2 and through which the inlet opening Ca1 and the outlet opening Ca2 communicate with each other. Therefore, even if the membrane member M is displaced to such a position as to come into contact with the inner surface of the liquid-phase-portion case Ca, the connecting recess Ca3 provides a flow route for the liquid between the inlet opening Ca1 and the outlet opening Ca2.

As illustrated in FIG. 11, the flow-route portion C1a of the inlet port C1 and the flow-route portion C2a of the outlet port C2 according to the present embodiment are configured such that the incoming direction α and the outgoing direction β of the liquid are offset from each other. Specifically, as illustrated in the drawing, the flow-route portion C1a of the inlet port C1 is configured such that the incoming direction α of the liquid is inclined downward toward the liquid-phase portion S1, and the flow-route portion C2a of the outlet port C2 is configured such that the outgoing direction β of the liquid is offset from the incoming direction α of the liquid (the two directions are not aligned with each other).

In the present embodiment, as illustrated in FIG. 11, the inlet port C1 and the outlet port C2 are each configured such that a virtual line Lb connecting a first center point Pa as the center position of the flow-route portion (C1a, C2a) in a boundary plane X1 defined between the flow-route portion (C1a, C2a) and the connecting portion (C1b, C2b) and a second center point Pb as the center position of the flow-route portion (C1a, C2a) in a plane X2 extending parallel to the boundary plane X1 and containing the opening edge of the inlet opening Ca1 or the outlet opening Ca2 is inclined with respect to a center line La (the axis) of the connecting portion (C1b, C2b) in side view. In the present embodiment, the inlet port C1 and the outlet port C2 are both shaped as above. However, at least one of the inlet port C1 and the outlet port C2 only needs to be shaped as above.

As illustrated in FIG. 11, the flow-route portion C1a of the inlet port C1 and the flow-route portion C2a of the outlet port C2 according to the present embodiment each have a diameter gradually reduced toward the liquid-phase portion S1. Specifically, as illustrated in the drawing, the flow-route portion C1a of the inlet port C1 is configured such that a diameter d2 at a position near the liquid-phase portion S1 is smaller than a diameter d1 at a position near the connecting portion C1b, and the flow-route portion C2a of the outlet port C2 is configured such that a diameter d4 at a position near the liquid-phase portion S1 is smaller than a diameter d3 at a position near the connecting portion C2b.

In the present embodiment, the flow-route portion C1a of the inlet port C1 and the flow-route portion C2a of the outlet port C2 each have a diameter gradually reduced toward the liquid-phase portion S1. However, at least the flow-route portion C1a of the inlet port C1 only needs to have a diameter gradually reduced toward the liquid-phase portion S1. That is, the flow-route portion C2a of the outlet port C2 may not necessarily have a gradually reduced diameter. If at least the flow-route portion C1a of the inlet port C1 has a diameter gradually reduced toward the liquid-phase portion S1, the diameter may be reduced continuously as in the present embodiment or in a stepwise manner.

According to the present embodiment, at least one of the flow-route portion C1a of the inlet port C1 and the flow-route portion C2a of the outlet port C2 is configured such that the incoming direction α or the outgoing direction β of the liquid is inclined with respect to the attaching plane Q defined for the membrane member M. Therefore, while the increase in the capacity of the liquid-phase portion S1 is suppressed, the blood (liquid) in the liquid-phase portion S1 can be stirred satisfactorily. Furthermore, at least the flow-route portion C1a of the inlet port C1 has a diameter gradually reduced toward the liquid-phase portion S1. Therefore, the flow velocity of the blood (liquid) flowing into the liquid-phase portion S1 is increased. Thus, retention in the liquid-phase portion S1 can be suppressed assuredly. Furthermore, since at least the flow-route portion C1a of the inlet port C1 has a diameter gradually reduced toward the liquid-phase portion S1, a vortex can be caused in the liquid-phase portion S1 while the flow velocity of the blood (liquid) flowing into the liquid-phase portion S1 is increased.

Furthermore, the inlet port C1 and the outlet port C2 according to the present embodiment project in such a manner as to form the predetermined angle f with respect to each other in the circumferential direction of the case C (the liquid-phase-portion case Ca). Therefore, while the increase in the capacity of the liquid-phase portion S1 is suppressed further, the inlet opening Ca1 and the outlet opening Ca2 can be prevented from facing each other. Thus, the effect of stirring the blood (liquid) in the liquid-phase portion S1 can be increased further.

Furthermore, the flow-route portion C1a of the inlet port C1 and the flow-route portion C2a of the outlet port C2 according to the present embodiment are configured such that the incoming direction α and the outgoing direction β of the liquid are offset from each other. Therefore, while the increase in the capacity of the liquid-phase portion S1 is suppressed further, the effect of stirring the blood (liquid) in the liquid-phase portion S1 can be increased further.

Furthermore, the case C according to the present embodiment includes the liquid-phase-portion case Ca defining the liquid-phase portion S1, and the gas-phase-portion case Cb defining the gas-phase portion S2. Furthermore, the attaching plane Q defined for the membrane member M is the virtual plane containing the holding surface (m1, m2) where the membrane member M is held between the liquid-phase-portion case Ca and the gas-phase-portion case Cb that are mated to each other. Therefore, the inlet port C1 or the outlet port C2 can be made accurately inclined with respect to the attaching plane Q.

Furthermore, at least one of the inlet port C1 and the outlet port C2 is configured such that the virtual line Lb connecting the first center point Pa as the center position of the flow-route portion (C1a, C2a) in the boundary plane X1 defined between the flow-route portion (C1a, C2a) and the connecting portion (C1b, C2b) and the second center point Pb as the center position of the flow-route portion (C1a, C2a) in the plane X2 extending parallel to the boundary plane X1 and containing the opening edge of the inlet opening Ca1 or the outlet opening Ca2 is inclined with respect to the center line La of the connecting portion (C1b, C2b). Therefore, the effect of stirring the liquid in the liquid-phase portion S1 can be increased further. Furthermore, according to the present embodiment, a blood circuit producing the above advantageous effects of the pressure detector 10 can be provided.

Now, a pressure detector according to a second embodiment of the present invention will be described.

The pressure detector according to the present embodiment is applied to the same blood purification apparatus as that of the first embodiment. As illustrated in FIG. 1, the pressure detector is connected to the venous blood circuit 2 at a position between the dialyzer 3 and the air-trap chamber 5 and is capable of detecting the pressure of the blood flowing in the venous blood circuit 2 (the blood circuit).

As illustrated in FIGS. 12 to 14, a pressure detector 10 according to the present embodiment includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P. Elements that are the same as those described in the first embodiment are denoted by corresponding ones of the reference numerals, and detailed description of those elements is omitted.

An inlet port C4 according to the present embodiment is a portion (a projected portion) connectable to the flow route for liquid (the blood circuit) and includes, as illustrated in FIG. 14, a flow-route portion C4a through which the liquid (blood) flows into an inlet opening Ca1 of the liquid-phase portion S1, and a connecting portion C4b connectable to the flow route (the blood circuit). Specifically, the flow-route portion C4a and the connecting portion C4b are continuous with each other in the axial direction thereof in the projected portion forming the inlet port C4. When a tube forming the flow route is connected to the connecting portion C4b, the liquid in the flow route can be made to flow into the flow-route portion C4a and then into the liquid-phase portion S1 through the inlet opening Ca1. Note that the inlet port C4 may be shaped as a recess to which the tube forming the flow route is to be connected.

An outlet port C5 according to the present embodiment is a portion (a projected portion) connectable to the flow route for liquid (the blood circuit) and includes, as illustrated in the drawing, a flow-route portion C5a through which the liquid (blood) having flowed into the liquid-phase portion S1 is discharged from an outlet opening Ca2, and a connecting portion C5b connectable to the flow route (the blood circuit). Specifically, the flow-route portion C5a and the connecting portion C5b are continuous with each other in the axial direction thereof in the projected portion forming the outlet port C5. When a tube forming the flow route is connected to the connecting portion C5b, the liquid having flowed into the liquid-phase portion S1 can be made to flow into the flow-route portion C5a and then to be discharged to a flow route (the blood circuit) on the downstream side. Note that the outlet port C5 may be shaped as a recess to which the tube forming the flow route is to be connected.

As with the case of the first embodiment, the flow-route portion C4a of the inlet port C4 and the flow-route portion C5a of the outlet port C5 according to the present embodiment are set such that, as illustrated in FIG. 14, the incoming direction α and the outgoing direction β of the liquid are inclined with respect to the attaching plane Q defined for the membrane member M. Specifically, the attaching plane Q according to the present embodiment is a virtual plane containing the holding surface m2 that holds the membrane member M. With reference to the attaching plane Q, the flow-route portion C4a of the inlet port C4 allows the liquid to flow in a direction (the incoming direction α) inclined downward from the connecting portion C4b toward the liquid-phase portion S1, and the flow-route portion C5a of the outlet port C5 allows the liquid to be discharged in a direction (the outgoing direction β) inclined downward from the liquid-phase portion S1 toward the connecting portion C5b.

In the present embodiment, the flow-route portion C4a of the inlet port C4 and the flow-route portion C5a of the outlet port C5 are configured such that the incoming direction α and the outgoing direction β of the liquid are inclined with respect to the attaching plane Q defined for the membrane member M. Note that at least one of the flow-route portion C4a of the inlet port C4 and the flow-route portion C5a of the outlet port C5 only needs to be configured such that the incoming direction α or the outgoing direction β of the liquid is inclined with respect to the attaching plane Q defined for the membrane member M.

Furthermore, as illustrated in FIG. 14, the flow-route portion C4a of the inlet port C4 and the flow-route portion C5a of the outlet port C5 according to the present embodiment are configured such that the incoming direction α and the outgoing direction β of the liquid are offset from each other and the amount of offset gradually increases toward the liquid-phase portion S1. Specifically, as illustrated in the drawing, the flow-route portion C4a of the inlet port C4 is configured such that the incoming direction α of the liquid is inclined downward toward the liquid-phase portion S1, and the flow-route portion C5a of the outlet port C5 is configured such that the outgoing direction β of the liquid is offset from the incoming direction α of the liquid and is inclined upward toward the liquid-phase portion S1. Thus, the amount of offset between the incoming direction α and the outgoing direction β gradually increases toward the liquid-phase portion S1.

According to the present embodiment, at least one of the flow-route portion C4a of the inlet port C4 and the flow-route portion C5a of the outlet port C5 is configured such that the incoming direction α or the outgoing direction β of the liquid is inclined with respect to the attaching plane Q defined for the membrane member M. Therefore, while the increase in the capacity of the liquid-phase portion S1 is suppressed, the blood (liquid) in the liquid-phase portion S1 can be stirred satisfactorily. Furthermore, the flow-route portion C4a of the inlet port C4 and the flow-route portion C5a of the outlet port C5 according to the present embodiment are configured such that the incoming direction α and the outgoing direction β of the liquid are offset from each other and the amount of offset gradually increases toward the liquid-phase portion S1. Therefore, while the increase in the capacity of the liquid-phase portion S1 is suppressed further, the distance between the inlet opening Ca1 and the outlet opening Ca2 can be increased. Thus, the effect of stirring the blood (liquid) in the liquid-phase portion S1 can be increased further.

Furthermore, the case C according to the present embodiment includes the liquid-phase-portion case Ca defining the liquid-phase portion S1, and the gas-phase-portion case Cb defining the gas-phase portion S2. Furthermore, the attaching plane Q defined for the membrane member M is the virtual plane containing the holding surface (m1, m2) where the membrane member M is held between the liquid-phase-portion case Ca and the gas-phase-portion case Cb that are mated to each other. Therefore, the inlet port C4 or the outlet port C5 can be made accurately inclined with respect to the attaching plane Q. Furthermore, according to the present embodiment, a blood circuit producing the above advantageous effects of the pressure detector 10 can be provided.

Now, a pressure detector according to a third embodiment of the present invention will be described.

The pressure detector according to the present embodiment is applied to the same blood purification apparatus as those of the first and second embodiments. As illustrated in FIG. 1, the pressure detector is connected to the venous blood circuit 2 at a position between the dialyzer 3 and the air-trap chamber 5 and is capable of detecting the pressure of the blood flowing in the venous blood circuit 2 (the blood circuit).

As illustrated in FIGS. 15 and 16, a pressure detector 10 according to the present embodiment includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P. Elements that are the same as those described in the first embodiment are denoted by corresponding ones of the reference numerals, and detailed description of those elements is omitted.

In the present embodiment, the flow-route portion C1a of the inlet port C1 and the flow-route portion C2a of the outlet port C2 each have a substantially constant diameter from one end to the other end thereof. The inlet port C1 and the outlet port C2 are each configured such that a virtual line Lb connecting a first center point Pa as the center position of the flow-route portion (C1a, C2a) in a boundary plane X1 defined between the flow-route portion (C1a, C2a) and the connecting portion (C1b, C2b) and a second center point Pb as the center position of the flow-route portion (C1a, C2a) in a plane X2 extending parallel to the boundary plane X1 and containing the opening edge of the inlet opening Ca1 or the outlet opening Ca2 is inclined with respect to a center line La (the axis) of the connecting portion (C1b, C2b). In the present embodiment, the inlet port C1 and the outlet port C2 are both shaped as above. However, at least one of the inlet port C1 and the outlet port C2 only needs to be shaped as above.

According to the present embodiment, at least one of the flow-route portion C1a of the inlet port C1 and the flow-route portion C2a of the outlet port C2 is configured such that the incoming direction α or the outgoing direction β of the liquid is inclined with respect to the attaching plane Q defined for the membrane member M. Therefore, while the increase in the capacity of the liquid-phase portion S1 is suppressed, the blood (liquid) in the liquid-phase portion S1 can be stirred satisfactorily. In particular, at least one of the inlet port C1 and the outlet port C2 is configured such that the virtual line Lb connecting the first center point Pa as the center position of the flow-route portion (C1a,C2a) in the boundary plane X1 defined between the flow-route portion (C1a, C2a) and the connecting portion (C1b, C2b) and the second center point Pb as the center position of the flow-route portion (C1a, C2a) in the plane X2 extending parallel to the boundary plane X1 and containing the opening edge of the inlet opening Ca1 or the outlet opening Ca2 is inclined with respect to the center line La of the connecting portion (C1b, C2b). Therefore, the effect of stirring the liquid in the liquid-phase portion S1 can be increased further.

Now, a pressure detector according to a fourth embodiment of the present invention will be described.

The pressure detector according to the present embodiment is applied to the same blood purification apparatus as those of the first to third embodiments. As illustrated in FIG. 1, the pressure detector is connected to the venous blood circuit 2 at a position between the dialyzer 3 and the air-trap chamber 5 and is capable of detecting the pressure of the blood flowing in the venous blood circuit 2 (the blood circuit).

As illustrated in FIGS. 17 and 18, a pressure detector 10 according to the present embodiment includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P. Elements that are the same as those described in the first embodiment are denoted by corresponding ones of the reference numerals, and detailed description of those elements is omitted.

In the present embodiment, as illustrated in FIG. 18, the flow-route portion C1a of the inlet port C1 or the flow-route portion C2a of the outlet port C2 is configured such that the incoming direction α or the outgoing direction β of the liquid is parallel to the attaching plane Q defined for the membrane member M, and such that an extension of a virtual line Lb connecting a first center point Pa as the center position of the flow-route portion (C1a, C2a) in a boundary plane X1 defined between the flow-route portion (C1a, C2a) and the connecting portion (C1b, C2b) of one of the inlet port C1 and the outlet port C2 and a second center point Pb as the center position of the flow-route portion (C1a, C2a) in a plane X2 extending parallel to the boundary plane X1 and containing the opening edge of the inlet opening Ca1 or the outlet opening Ca2 does not pass through the second center point Pb of the other of the inlet port C1 and the outlet port C2 in plan view.

Furthermore, as illustrated in FIG. 18, the flow-route portion C1a of the inlet port C1 and the flow-route portion C2a of the outlet port C2 according to the present embodiment each have a diameter gradually reduced toward the liquid-phase portion S1. Specifically, as illustrated in the drawing, the flow-route portion C1a of the inlet port C1 is configured such that a diameter at a position near the liquid-phase portion S1 is smaller than a diameter at a position near the connecting portion C1b, and the flow-route portion C2a of the outlet port C2 is configured such that a diameter at a position near the liquid-phase portion S1 is smaller than a diameter at a position near the connecting portion C2b.

In the present embodiment, the flow-route portion C1a of the inlet port C1 and the flow-route portion C2a of the outlet port C2 each have a diameter gradually reduced toward the liquid-phase portion S1. However, at least the flow-route portion C1a of the inlet port C1 only needs to have a diameter gradually reduced toward the liquid-phase portion S1. That is, the flow-route portion C2a of the outlet port C2 may not necessarily have a gradually reduced diameter. If at least the flow-route portion C1a of the inlet port C1 has a diameter gradually reduced toward the liquid-phase portion S1, the diameter may be reduced continuously as in the present embodiment or in a stepwise manner.

According to the present embodiment, the flow-route portion C1a of the inlet port C1 or the flow-route portion C2a of the outlet port C2 is configured such that the incoming direction α or the outgoing direction β of the liquid is parallel to the attaching plane Q defined for the membrane member M, and such that the extension of the virtual line Lb connecting the first center point Pa as the center position of the flow-route portion (C1a, C2a) in the boundary plane X1 defined between the flow-route portion (C1a, C2a) and the connecting portion (C1b, C2b) of one of the inlet port C1 and the outlet port C2 and the second center point Pb as the center position of the flow-route portion (C1a, C2a) in the plane X2 extending parallel to the boundary plane X1 and containing the opening edge of the inlet opening Ca1 or the outlet opening Ca2 does not pass through the second center point Pb of the other of the inlet port C1 and the outlet port C2. Therefore, while the increase in the capacity of the liquid-phase portion S1 is suppressed, the liquid in the liquid-phase portion S1 can be stirred satisfactorily. In particular, at least the flow-route portion C1a of the inlet port C1 has a diameter gradually reduced toward the liquid-phase portion S1. Therefore, the flow velocity of the liquid flowing into the liquid-phase portion S1 is increased. Thus, retention in the liquid-phase portion S1 can be suppressed assuredly.

Now, a pressure detector according to a fifth embodiment of the present invention will be described.

The pressure detector according to the present embodiment is applied to the same blood purification apparatus as those of the first to fourth embodiments. As illustrated in FIG. 1, the pressure detector is connected to the venous blood circuit 2 at a position between the dialyzer 3 and the air-trap chamber 5 and is capable of detecting the pressure of the blood flowing in the venous blood circuit 2 (the blood circuit).

As illustrated in FIGS. 19 and 20, a pressure detector 10 according to the present embodiment includes a case C connectable to the flow route for liquid (in the present embodiment, the venous blood circuit 2 (the blood circuit)), and a membrane member M provided in the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P. Elements that are the same as those described in the first embodiment are denoted by corresponding ones of the reference numerals, and detailed description of those elements is omitted.

In the present embodiment, as illustrated in FIG. 20, the flow-route portion C1a of the inlet port C1 or the flow-route portion C2a of the outlet port C2 is configured such that the incoming direction α or the outgoing direction β of the liquid is parallel to the attaching plane Q defined for the membrane member M, and such that an extension of a virtual line Lb connecting a first center point Pa as the center position of the flow-route portion (C1a, C2a) in a boundary plane X1 defined between the flow-route portion (C1a, C2a) and the connecting portion (C1b, C2b) of one of the inlet port C1 and the outlet port C2 and a second center point Pb as the center position of the flow-route portion (C1a, C2a) in a plane X2 extending parallel to the boundary plane X1 and containing the opening edge of the inlet opening Ca1 or the outlet opening Ca2 does not pass through the second center point Pb of the other of the inlet port C1 and the outlet port C2 in plan view.

According to the present embodiment, the flow-route portion C1a of the inlet port C1 or the flow-route portion C2a of the outlet port C2 is configured such that the incoming direction α or the outgoing direction β of the liquid is parallel to the attaching plane Q defined for the membrane member M, and such that the extension of the virtual line Lb connecting the first center point Pa as the center position of the flow-route portion (C1a, C2a) in the boundary plane X1 defined between the flow-route portion (C1a, C2a) and the connecting portion (C1b, C2b) of one of the inlet port C1 and the outlet port C2 and the second center point Pb as the center position of the flow-route portion (C1a, C2a) in the plane X2 extending parallel to the boundary plane X1 and containing the opening edge of the inlet opening Ca1 or the outlet opening Ca2 does not pass through the second center point Pb of the other of the inlet port C1 and the outlet port C2. Therefore, while the increase in the capacity of the liquid-phase portion S1 is suppressed, the liquid in the liquid-phase portion S1 can be stirred satisfactorily.

While the embodiments have been described above, the present invention is not limited thereto. The pressure detector 10 may be connected to another position of the blood circuit (for example, a position of the arterial blood circuit 1 between the distal end and the blood pump 4, or a position of the arterial blood circuit 1 between the blood pump 4 and the dialyzer 3). The blood circuit to which the present pressure detector 10 is to be connected may be in another type. For example, the blood circuit may be provided with not the air-trap chamber 5 but the present pressure detector 10 instead.

Moreover, while the above embodiments concern a case where the gas-phase-portion case Cb has the recesses Cb4 surrounding the opening Cb1 with the hydrophobic membrane B covering the recesses Cb4 inclusive of the opening Cb1, the recesses Cb4 and the hydrophobic membrane B may be omitted. Furthermore, while the above embodiments concern a case where the plurality of ribs Cb2 are arranged radially about the opening Cb1, the ribs Cb2 may be omitted, or another irregular pattern may be provided.

While the above embodiments each concern the pressure detector 10 provided to the blood circuit intended for dialysis treatment, the present invention may be applied to a pressure detector provided to another blood circuit to be used in a treatment of purifying blood of a patient. For example, the present invention may be applied to a pressure detector provided to a blood circuit to be used in acetate-free biofiltration (AFBF), continuous slow hemofiltration, hemoadsorption, selective cytapheresis, plasma exchange, double filtration plasmapheresis, plasma adsorption, or the like.

The present invention is applicable to any pressure detector of any other type or for any other usage, as long as at least one of a flow-route portion of an inlet port and a flow-route portion of an outlet port is configured such that an incoming direction or an outgoing direction of liquid is inclined with respect to an attaching plane defined for a membrane member.

REFERENCE SIGN LIST 1 arterial blood circuit
2 venous blood circuit
3 dialyzer (blood purifier)
4 blood pump
5 air-trap chamber
6 dialysis device
7 storage unit
8 air-trap chamber
9 clamp unit
10 pressure detector
L1 dialysate introduction line
L2 dialysate drain line
L3 physiological-saline supply line
C case
Ca liquid-phase-portion case
Ca1 inlet opening
Ca2 outlet opening
Cb gas-phase-portion case
Cb1 opening
C1 inlet port
C1a flow-route portion
C1b connecting portion
C2 outlet port
C2a flow-route portion
C2b connecting portion
C3 connection port
M membrane member
P pressure detection sensor
S1 liquid-phase portion
S2 gas-phase portion
K pipe
B hydrophobic membrane
Q (Q1, Q2, Q3) attaching plane
Pa first center point
Pb second center point
X1 boundary plane between flow-route portion and connecting portion
X2 plane parallel to boundary plane X1

The invention claimed is:

1. A pressure detector comprising:
a case connectable to a flow route for liquid, and
a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion,
the pressure detector detecting the pressure of the liquid in the flow route by detecting a pressure in the gas-phase portion, the pressure detector comprising:
an inlet port including an inlet connecting portion connectable to the flow route for the liquid, and an inlet flow-route portion through which the liquid flows into an inlet opening of the liquid-phase portion; and
an outlet port including an outlet connecting portion connectable to the flow route for the liquid, and an outlet flow-route portion through which the liquid having flowed into the liquid-phase portion is discharged from an outlet opening,
wherein at least one of the inlet flow-route portion of the inlet port and the outlet flow-route portion of the outlet port is configured such that an incoming direction or an outgoing direction of the liquid is inclined with respect to an attaching plane defined for the membrane member; and
wherein a first virtual line extends along a center portion of the inlet connecting portion to a first center point, and an inlet center line extends through an inlet center portion of the inlet flow-route portion from the first center point at an incline relative to the first virtual line; or
wherein a second virtual line extends along a center portion of the outlet connecting portion to a second center point, and an outlet center line extends through an outlet center portion of the outlet flow-route portion from the second center point at an incline relative to the second virtual line.

2. A pressure detector comprising:
a case connectable to a flow route for liquid, and
a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion,
the pressure detector detecting the pressure of the liquid in the flow route by detecting a pressure in the gas-phase portion, the pressure detector comprising:
an inlet port including an inlet connecting portion connectable to the flow route for the liquid, and an inlet flow-route portion through which the liquid flows into an inlet opening of the liquid-phase portion, wherein at least the inlet flow-route portion of the inlet port has a diameter gradually reduced toward the liquid-phase portion; and
an outlet port including an outlet connecting portion connectable to the flow route for the liquid, and an outlet flow-route portion through which the liquid having flowed into the liquid-phase portion is discharged from an outlet opening,
wherein at least one of the inlet flow-route portion of the inlet port and the outlet flow-route portion of the outlet port is configured such that an incoming direction or an outgoing direction of the liquid is inclined with respect to an attaching plane defined for the membrane member;
wherein a first virtual line extends along a center portion of the inlet connecting portion to a first center point, and an inlet center line extends through an inlet center portion of the inlet flow-route portion from the first center point at an incline relative to the first virtual line; or
wherein a second virtual line extends along a center portion of the outlet connecting portion to a second center point, and an outlet center line extends through an outlet center portion of the outlet flow-route portion from the second center point at an incline relative to the second virtual line.

3. The pressure detector according to claim 1, wherein the inlet port and the outlet port form a predetermined angle with respect to each other in a circumferential direction of the case.

4. The pressure detector according to claim 1, wherein the inlet flow-route portion of the inlet port and the outlet flow-route portion of the outlet port are configured such that the incoming direction and the outgoing direction of the liquid are offset from each other.

5. The pressure detector according to claim 1, wherein the case includes a liquid-phase-portion case defining the liquid-phase portion, and a gas-phase-portion case defining the gas-phase portion; and wherein the attaching plane defined for the membrane member is a virtual plane containing a holding surface where the membrane member is held between the liquid-phase-portion case and the gas-phase-portion case that are mated to each other.

6. The pressure detector according to claim 2,
wherein the first virtual line extends along the center portion of the inlet connecting portion to the first center point, and the inlet center line extends through the inlet center portion of the inlet flow-route portion from the first center point at the incline relative to the first virtual line; and
wherein the second virtual line extends along the center portion of the outlet connecting portion to the second center point, and the outlet center line extends through the outlet center portion of the outlet flow-route portion from the second center point at the incline relative to the second virtual line.

7. The pressure detector according to claim 1, wherein at least the inlet flow-route portion of the inlet port has a diameter gradually reduced toward the liquid-phase portion.

8. The pressure detector according to claim 1, wherein the inlet port and the outlet port form a predetermined angle with respect to each other in a circumferential direction of the case.

9. The pressure detector according to claim 1, wherein the inlet flow-route portion of the inlet port and the outlet flow-route portion of the outlet port are configured such that the incoming direction and the outgoing direction of the liquid are offset from each other.

10. The pressure detector according to claim 1, wherein the case includes a liquid-phase-portion case defining the liquid-phase portion, and a gas-phase-portion case defining the gas-phase portion; and wherein the attaching plane defined for the membrane member is a virtual plane containing a holding surface where the membrane member is held between the liquid-phase-portion case and the gas-phase-portion case that are mated to each other.

11. A blood circuit to which the pressure detector according to claim 1 is connected.

12. A blood circuit to which the pressure detector according to claim 1 is connected.

13. The pressure detector according to claim 1, wherein at least the inlet flow-route portion of the inlet port has a diameter gradually reduced toward the liquid-phase portion.

14. The pressure detector according to claim 2, wherein the inlet port and the outlet port form a predetermined angle with respect to each other in a circumferential direction of the case.

15. The pressure detector according to claim 2, wherein the inlet flow-route portion of the inlet port and the outlet flow-route portion of the outlet port are configured such that the incoming direction and the outgoing direction of the liquid are offset from each other.

16. The pressure detector according to claim 2, wherein the case includes a liquid-phase-portion case defining the liquid-phase portion, and a gas-phase-portion case defining the gas-phase portion; and wherein the attaching plane defined for the membrane member is a virtual plane containing a holding surface where the membrane member is held between the liquid-phase-portion case and the gas-phase-portion case that are mated to each other.

17. A blood circuit to which the pressure detector according to claim 2 is connected.

* * * * *